(12) United States Patent
Gross

(10) Patent No.: US 8,132,476 B2
(45) Date of Patent: Mar. 13, 2012

(54) METHOD AND APPARATUS FOR HANDLING SMALL QUANTITIES OF FLUIDS

(75) Inventor: Karl Gross, Fremont, CA (US)

(73) Assignee: Hy-Energy, LLC, Newark, CA (US)

( * ) Notice: Subject to any disclaimer, the term of this patent is extended or adjusted under 35 U.S.C. 154(b) by 538 days.

(21) Appl. No.: 11/424,867

(22) Filed: Jun. 17, 2006

(65) Prior Publication Data

US 2007/0000337 A1    Jan. 4, 2007

Related U.S. Application Data

(60) Provisional application No. 60/692,344, filed on Jun. 20, 2005, provisional application No. 60/803,655, filed on Jun. 1, 2006.

(51) Int. Cl.
*G01N 1/10* (2006.01)
(52) U.S. Cl. .................................................. 73/863.73
(58) Field of Classification Search ... 73/863.72–863.73
See application file for complete search history.

(56) References Cited

U.S. PATENT DOCUMENTS

| | | | |
|---|---|---|---|
| 3,530,721 A | 9/1970 | Hrdina | |
| 3,915,013 A * | 10/1975 | Gaeke | 73/863.72 |
| 4,030,369 A * | 6/1977 | Etheridge | 73/863.72 |
| 5,707,150 A * | 1/1998 | Sittler | 374/36 |
| 6,112,604 A | 9/2000 | Peterson | |
| 6,649,129 B1 * | 11/2003 | Neal | 422/89 |
| 2008/0253932 A1 * | 10/2008 | Gross | 422/88 |

* cited by examiner

*Primary Examiner* — Hezron E Williams
*Assistant Examiner* — Nashmiya Fayyaz
(74) *Attorney, Agent, or Firm* — Patterson & Sheridan, LLP

(57) ABSTRACT

The invention relates to a method and an apparatus for handling small quantities of fluids useful, for example, in measuring the gas and/or liquid sorption and desorption properties of substances such as hydrogen sorption by solid or liquid hydrogen storage materials. In one embodiment, low-volume rotary valves are used to dose samples in a sample holder. In another embodiment, a rotary valve is used as a dosing/bypass valve to both condition and measure samples. The invention also relates to an actuator for a rotary valve that has a manual override feature.

31 Claims, 16 Drawing Sheets

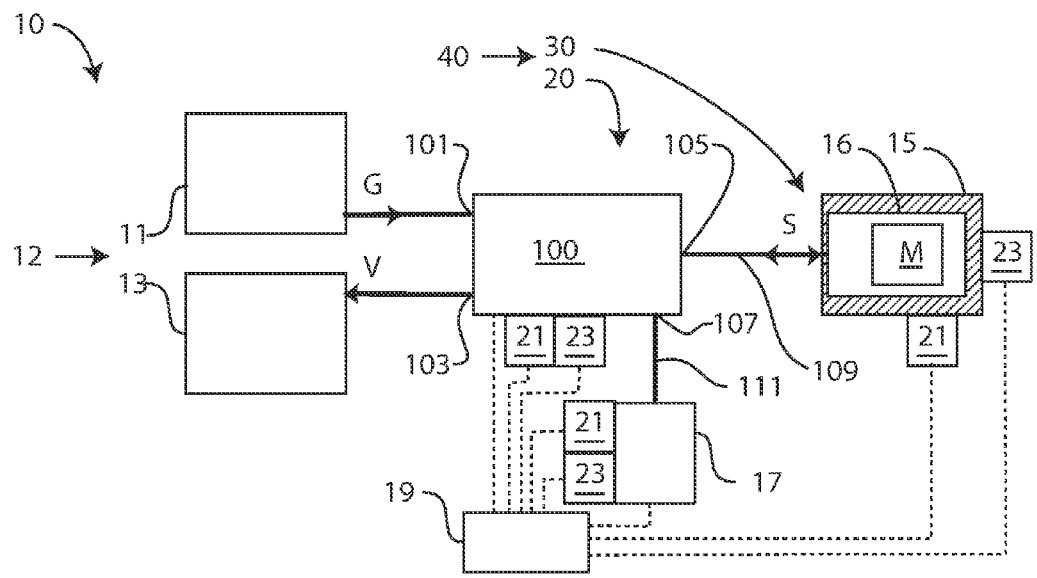
FIG. 1
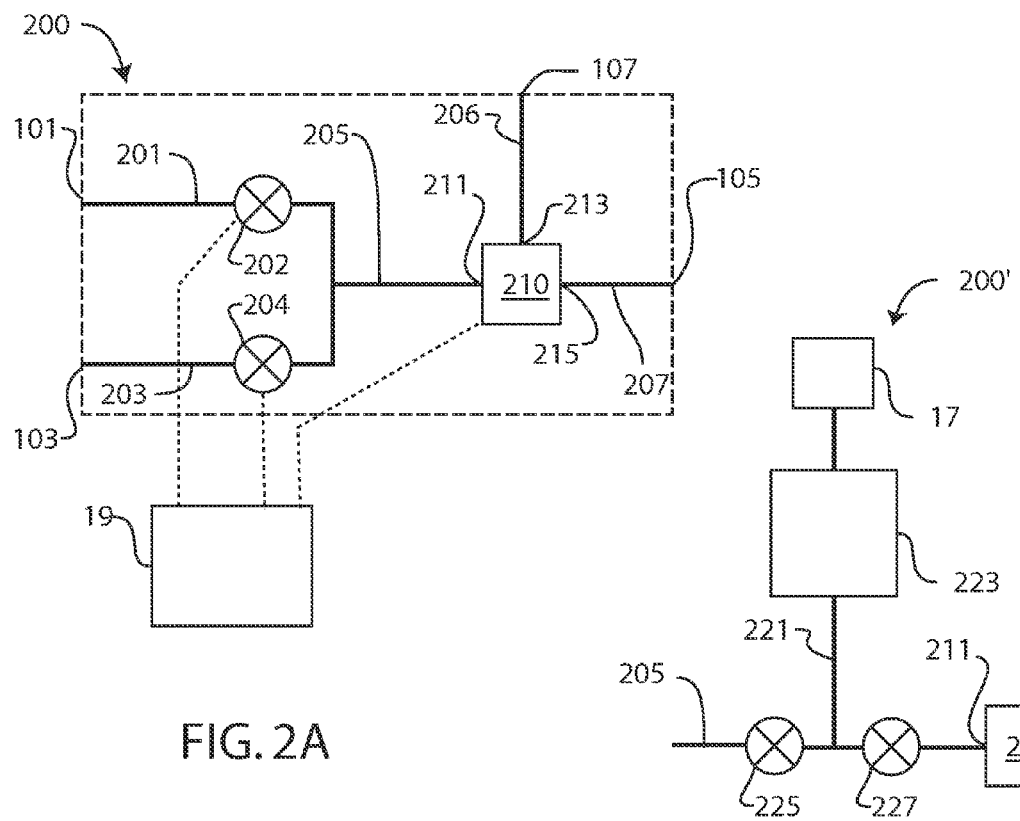
FIG. 2A
FIG. 2B

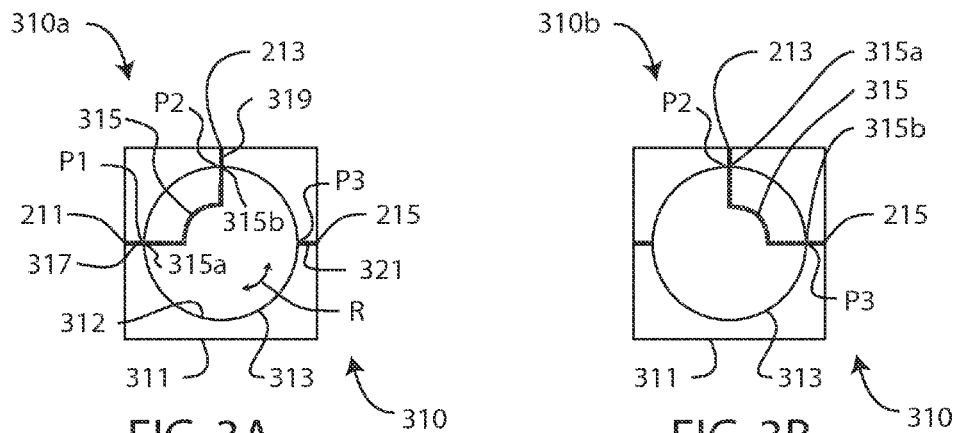
FIG. 3A
FIG. 3B
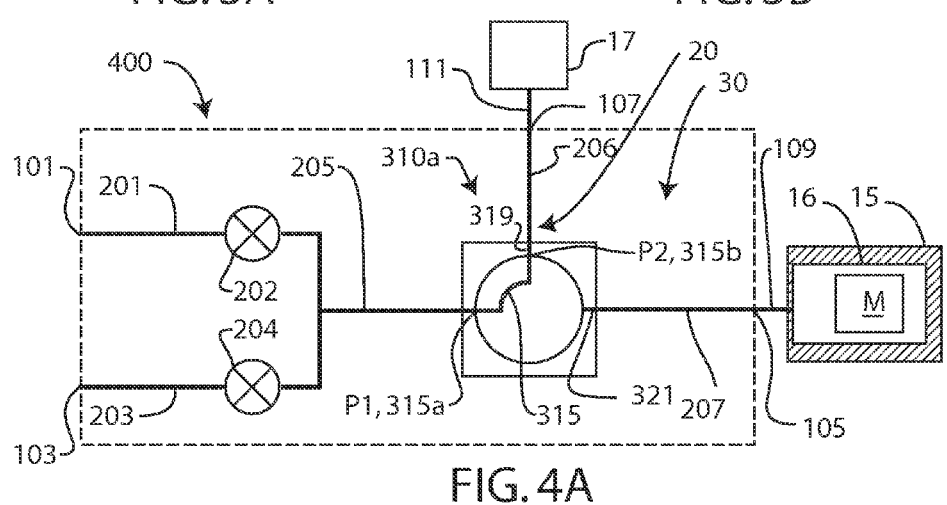
FIG. 4A
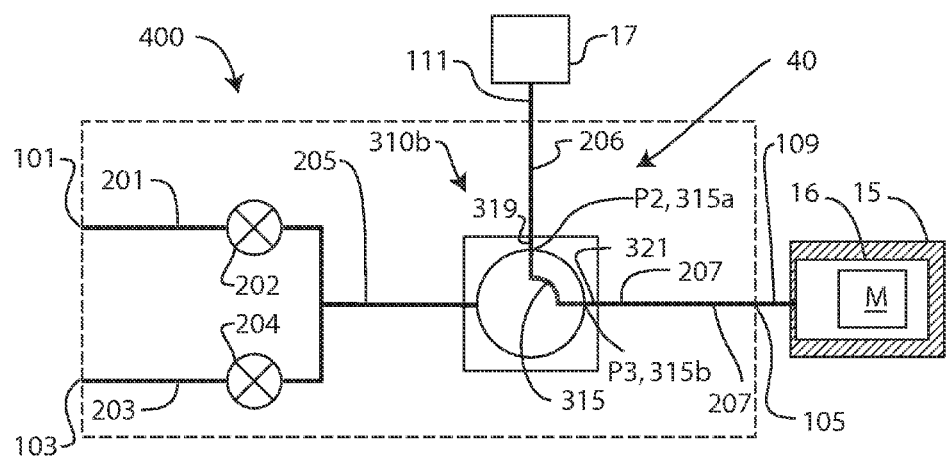
FIG. 4B

180
METHOD AND APPARATUS FOR HANDLING SMALL QUANTITIES OF FLUIDS

RELATED APPLICATIONS

This application claims the benefit under 35 U.S.C. §119 (e) of: U.S. Provisional Application No. 60/692,344, filed Jun. 20, 2005, titled METHOD AND APPARATUS FOR MEASURING SMALL QUANTITIES OF GAS OR LIQUID SORPTION AND DESORPTION PROPERTIES OF MATERIALS; and U.S. Provisional Application No. 60/803,655, filed Jun. 1, 2006, titled METHOD AND APPARATUS FOR HANDLING SMALL QUANTITIES OF GASES OR LIQUIDS. The entire contents of the above-listed provisional applications are hereby incorporated by reference herein and made part of this specification.

BACKGROUND

1. Field of the Invention

The present invention relates to handling devices for fluids, including but not limited to gases or liquids, and specifically to the control of small quantities of fluids and to devices for performing measurements on small quantities of gases or liquids.

2. Description of the Background

One common way to determine gas sorption properties of a material is to measure changes in pressure in a calibrated volume as gas is sorbed by a test sample of the material. The quantity of gas sorbed in each measurement is found from the equation of state of the gas. It is necessary to know three parameters to determine the quantity of gas sorbed: the pressure, temperature and volume of the gas. At constant volume and temperature, the quantity of gas sorbed is determined by measuring the change in pressure. From a known sample mass it is then possible to determine the mass concentration of gas that has been sorbed or desorbed by the sample. If the composition of the sample is well known, then the stoichiometry of gas in the sample may also be determined from the measured concentration.

Thus, for example, the pressure-composition-temperature characteristic curve (a "PCT" curve) of a sample may be obtained by dosing the sample with small "aliquots" of gas from a small volume or desorbed into a small volume such that only a small fraction of gas is sorbed or desorbed at one time. A sorption PCT curve is measured by increasing the pressure in each aliquot of gas applied to the sample in a step-wise fashion. Similarly, a desorption PCT diagram is measured by decreasing the pressure in a step-wise fashion, in the small volume into which the sample is desorbed. The conventional apparatus for performing such measurements is referred to as a Sieverts' device.

Typically, a gas dosing apparatus or Sieverts device involves dosing gas from a known volume using standard orifice and seal valves or on/off valves. Common examples of the types of valves are diaphragm valves or needle valves. These valves may be automated using pneumatic plungers or electrical solenoid mechanisms. One problem with these types of valves is that the diaphragm or stem moves in a lateral motion to open or close the valve, causing an internal volume change in the system as a whole. Volume changes on the order of 0.05 milliliters, for example, may cause significant measurement error if not taken into account when calculating the mass balance of a gas dosing system. This mass balance is critical when making specific types of measurements such quantifying the amount of gas sorption to or from a sample.

There are many problems and issues with conventional Sieverts' devices and with other prior art methods and devices for measuring sorption. Conventional devices must be operated for long periods of time taking many measurements, such as are required for generating a PCT curve. This may involve large numbers of repetitive operations, such as delivering aliquots in a PCT measurement, or switching between sorption and desorption in cycle-life measurements. It is important to obtain evenly spaced data points of sorption/desorption measurement along PCT curve. Without a detailed and even distribution of data points over the entire pressure range, the PCT curve will not be well resolved and certain portions may not be observed at all. Thus, for example, changes in the equilibrium plateau pressure identified with hydride phase transitions could be missed entirely.

Variations in air temperature in a room in which measurements are performed, or variations in the gas temperature throughout a measurement device, can produce significant errors in measuring the quantity of gases sorption or desorption from a material. Even if the surrounding air temperature is measured and introduced into the equation of state, the time lag between changes in the temperature of the surrounding air and the temperature of the gases in a Sieverts apparatus can be significant enough that the data can not be sufficiently corrected.

Small samples, such as those of 1 gram or less, and/or samples that adsorb or absorb only small quantities of gas, for example 50 milliliters STP or less, are difficult to investigate using typical volumetric devices that often have calibrated volumes and piping with volumes on the order of 10 milliliters or more. Thus, for example, standard on/off valves have internal volumes greater than 1 milliliter, especially when designed to operate at pressures greater than 30 atmospheres. However, to be able to measure gas sorption on very small samples using the Sieverts method, very small dosing volumes are required. For example, a pressure concentration temperature isotherm measurement on a 20 mg sample with 1 weight percent gas uptake under ambient conditions would require a dosing volume on the order of 0.5 milliliters. This is much smaller that the standard valves' internal volume, without even considering the volume of any tubing, pressure transducers, or fittings.

Manual orifice-and-seat-type valves found in prior art devices are subject to inconsistent operator behavior. In particular, operators have a tendency to over-tighten valves during high-pressure experiments, resulting in valve seat damage causing the valve to leak. Manual systems have been known to operate for only a few experiments before the valves leak to the point that the data is seriously compromised.

Thus there is a need in the art for a method and apparatus that permits the accurate measurement of sorption characteristics using small quantities of sorption materials. The apparatus should preferably be easily automated, capable of operation at constant or measurable temperatures, and having repeatable volumes. There is also a need in the art for a dosing valve and other system components have very small internal volumes.

BRIEF SUMMARY OF THE INVENTION

The present invention overcomes some of the problems of prior art valves and sorption measurement devices by providing an apparatus having a small dosing volume. In one embodiment, the apparatus is a measurement device. In another embodiment, the apparatus is a valve for dosing small quantities of fluid.

It is one aspect of the present invention to provide an automated apparatus that employs computer controlled operations and data collection.

It is another aspect of the present invention to provide an apparatus having a small dosing volume for dosing small quantities of gases and/or liquids using a rotary valve.

It is one aspect of the present invention to provide an apparatus having a combined dosing and bypass function.

It is yet another aspect of the present invention to provide an apparatus having a small dosing volume with small gas vessels, spacers, and small internal diameter gas lines (c.a. 0.15 mm diameter) to reduce the minimum working volumes to about 0.1 to 10 milliliters. This enables the measurement of gas sorption properties of small (<1 gram) samples and samples with limited gas sorption capacities. In various embodiment the dosing volume is approximately 0.01 milliliters, is less than approximately 0.05 milliliters, is less than approximately 0.1 milliliters, is less than approximately 0.5 milliliters, is less than approximately 1.0 milliliters, is less than approximately 5.0 milliliters, or is less than 1.0 liters It is one aspect of the present invention to provide an apparatus having a small dosing volume to measure the sorption and desorption properties of a materials capable of gas or liquid sorption. In some embodiments, the apparatus is an apparatus for measuring the hydrogen adsorbing, absorbing or desorbing properties of hydrogen absorbing metal alloys or other compounds, hydrogen, oxygen, nitrogen, carbon-dioxide, methane and other gas adsorbing carbon materials, chemical compounds, and high-surface area absorbing substances.

It is another aspect of the present invention to provide an apparatus having a small dosing volume that can be attached to one of many different types of gas/liquid analyzers, gas/liquid manifolds, and gas sorption/desorption isotherm measuring instruments. In another embodiment, the apparatus performs measurement by applying precise aliquots of gas or liquid using an automatic rotary valve that can dose small quantities of gas or liquid (ca, 0.01 to 500 sml depending on the dosing volume and pressure). In yet another embodiment, the apparatus measures without a system volume change by dosing with a rotary valve, greatly improving the accuracy of gas/liquid uptake and release measurements.

It is yet another aspect of the present invention to provide an automated apparatus and method of measuring gas adsorption, absorption and desorption in materials.

It is one aspect of the present invention to provide an apparatus that may be attached to a gas or liquid manifold or any number of gas or liquid analyzing instruments.

It is another aspect of the present invention to provide better apparatus for measuring gas or liquid sorption and desorption properties of small samples of materials by dosing the sample with small quantities of gas or liquids.

It is yet another aspect of the present invention to provide an apparatus that has no change in system volume on filling a reservoir with a gas or a liquid and subsequently dosing the gas or liquid to a sample for sorption or desorption.

It is yet another aspect of the present invention to provide an apparatus having a rotary valve with a small slit in a plastic member that conducts gas from one port on a rotary valve to the next port. To switch between gas ports on the valve, parts of the rotary valve are rotated by either manually or automatically until the slit is aligned with a second set of ports. Because the valve opens and closes by rotating the sealing surfaces, there is no volume change associated with opening or closing the valve. In one embodiment, the slit and all gas connections are all very small, with volumes on the order of 0.1 to 1.0 microliters, and may therefore be much smaller than the total calibrated reservoir volume required for dosing.

It is one aspect to provide an apparatus connectable to a source of fluid or vacuum. The apparatus includes a sample holder having an internal volume, a dosing reservoir, and a valve having at least two ports and at least two positions. The at least two ports includes a first port fluidly connectable to the source, and a second port fluidly connected to the internal volume. The at least two positions includes a first position that fluidly connects the first port and the dosing reservoir, and defines a first enclosed volume including the internal volume, and a second position that fluidly connects the dosing reservoir and the internal volume to form a second enclosed volume. In one embodiment the valve includes two or more fluidly connected valves.

It is another aspect to provide an apparatus connectable to a source of fluid or vacuum. The apparatus includes a sample holder having an internal volume, a dosing reservoir, and a valve having at least two ports and at least two positions. The at least two ports includes a first port fluidly connectable to the source, and a second port fluidly connected to the internal volume. The at least two positions includes a first position that fluidly connects the first port and the dosing reservoir, and defines a first enclosed volume including the internal volume, and a second position that fluidly connects the dosing reservoir and the internal volume to form a second enclosed volume. The apparatus further includes a pressure measuring device, at least three ports including a third port fluidly connected to the pressure measuring device. The first position fluidly connects the dosing reservoir, the pressure measuring device, and the dosing reservoir, and the second position fluidly connects the second enclosed volume and the pressure measuring device.

It is one aspect to provide an apparatus connectable to a source of fluid or vacuum. The apparatus includes a sample holder having an internal volume, a dosing reservoir, and a valve having at least two ports and at least two positions. The at least two ports includes a first port fluidly connectable to the source, and a second port fluidly connected to the internal volume. The at least two positions includes a first position that fluidly connects the first port and the dosing reservoir, and defines a first enclosed volume including the internal volume, and a second position that fluidly connects the dosing reservoir and the internal volume to form a second enclosed volume. The apparatus further includes a plurality of sources, a passageway to fluidly connect each of the plurality of sources and the first port, and a plurality of on/off valves to control fluid communication between each of the plurality of sources and the first port.

It is one aspect to provide an apparatus connectable to a source of fluid or vacuum. The apparatus includes a sample holder having an internal volume, a dosing reservoir, and a valve having at least two ports and at least two positions. The at least two ports includes a first port fluidly connectable to the source, and a second port fluidly connected to the internal volume. The at least two positions includes a first position that fluidly connects the first port and the dosing reservoir, and defines a first enclosed volume including the internal volume, and a second position that fluidly connects the dosing reservoir and the internal volume to form a second enclosed volume. The apparatus further includes a passageway to fluidly connectable to the source and the internal volume, and an on/off valve to control fluid communication between the source and the sample holder. In one embodiment the valve has at least three positions including a third position that fluidly connects the first port and the internal volume. In another embodiment, the at least three ports is at least four ports including a fourth port fluidly connectable to the source, and the third position fluidly connects the third port and the fourth port. In yet another embodiment, the at least three ports is at least four ports including a fourth port fluidly connected to the sample holder, with the third position fluidly connects the first port and the fourth port.

It is one aspect to provide an apparatus connectable to a source of fluid or vacuum. The apparatus includes a sample holder having an internal volume, a dosing reservoir, and a valve having at least two ports and at least two positions. The at least two ports includes a first port fluidly connectable to the source, and a second port fluidly connected to the internal volume. The at least two positions includes a first position that fluidly connects the first port and the dosing reservoir, and defines a first enclosed volume including the internal volume, and a second position that fluidly connects the dosing reservoir and the internal volume to form a second enclosed volume. The apparatus further includes an actuator operably engageable with the valve. In one embodiment, the actuator has a manual override to disengage the actuator and permit manual operation of the rotary valve.

It is another aspect of the present invention to provide a source of fluid or vacuum. The apparatus includes a sample holder having an internal volume, a dosing reservoir, and a valve having at least two ports and at least three positions. The at least two ports includes a first port fluidly connectable to the source, and a second port fluidly connected to the internal volume. The at least three positions includes a first position that fluidly connects the first port and the dosing reservoir, and defines a first enclosed volume including the internal volume, a second position that fluidly connects the dosing reservoir and the internal volume to form a second enclosed volume, and a third position that fluidly connects the first port and the internal volume.

It is an aspect of the present invention to provide device to measure sorption properties of a material sample, the device comprising: a sample holder having an internal volume for containing a material sample, a plurality of dosing reservoirs, and one or more valves operable to connect individual ones of the plurality of dosing reservoirs to the internal volume, each forming an enclosed volume.

It is an aspect of the present invention to provide a device to measure sorption properties of a material sample, the device comprising: a sample holder having an internal volume for containing a material sample, a dosing reservoir, a valve to fluidly connect the dosing reservoir and the internal volume to form an enclosed volume, two or more pressure measuring devices, and a valve to fluidly connect individual ones of the two or more pressure measuring devices to the internal volume.

It is one aspect of the present invention to provide an apparatus to control a rotary valve. The apparatus includes a frame, a mounting to attach the rotary valve to the frame, an actuator attached to the frame and operably engageable with a mounted rotary valve, and a manual override device to disengage the actuator and permit manual operation of the mounted rotary valve. In one embodiment, the actuator is a pneumatic actuator. In another embodiment, the actuator is an electric actuator. In yet another embodiment, the apparatus includes a computer system to control the rotary valve when operably engaged It is another aspect of the present invention to provide an apparatus to control a rotary valve. The apparatus includes a frame, a mounting to attach the rotary valve to the frame, an actuator attached to the frame and operably engageable with a mounted rotary valve, and a manual override device to disengage the actuator and permit manual operation of the mounted rotary valve. The rotary valve includes a rotatable member for operating the rotary valve, and the actuator includes a first member having a first end adapted to be connected to the rotatable member of the mounted rotary valve and a second end, and a knob attached to the second end. When the knob rotates upon rotation of the rotatable member of the mounted rotary valve. In one embodiment, the actuator includes a second member engageable with the first member, and the manual override device disengages the actuator by disengaging the first member and the second member. The manual override device may also includes a button that, when pushed, separates the interlocking portions of the first and second member.

These aspects, together with the various ancillary aspects, will become apparent to those skilled in the art from the following detailed description, are attained by the apparatus and methods of the present invention, embodiments thereof being shown with reference to the accompanying drawings, by way of example only, wherein:

BRIEF DESCRIPTION OF THE SEVERAL VIEWS OF THE DRAWING

FIG. 1 is a schematic of a measurement apparatus of the present invention;

FIG. 2A is a schematic diagram of a first embodiment valve system of the present invention;

FIG. 2B is a schematic diagram of detail of an alternative embodiment valve system of the present invention;

FIGS. 3A and 3B are schematic diagrams of a first embodiment of a rotary valve for use with valve systems of the present invention as a three-port, two-position valve, where FIG. 3A shows the rotary valve in a first position and FIG. 3B shows the rotary valve in a second position;

FIGS. 4A and 4B are schematic diagrams of the valve system of FIG. 2A or 2B incorporating the rotary valves of FIGS. 3A and 3B, respectively;

FIG. 6A shows the rotary valve in a first position and FIG. 6B shows the rotary valve in a second position;

FIGS. 10A, 10B, 10C, and 10D show the rotary valve in a first, second, third, and fourth position, respectively;

Figure 5:
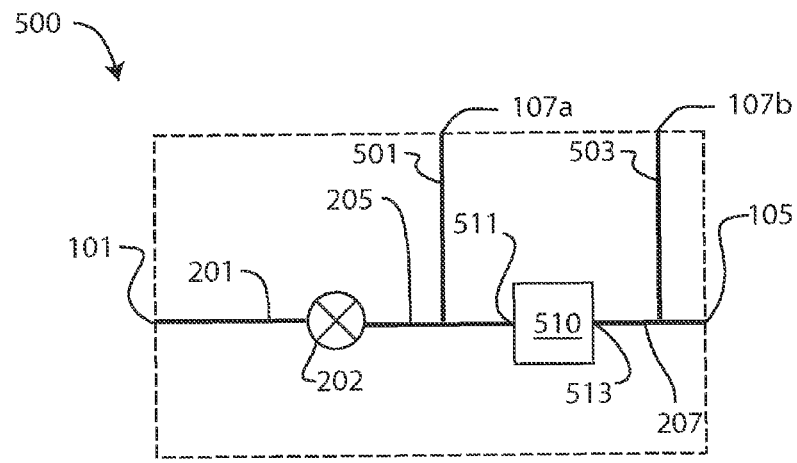
FIG. 5 is a schematic of an alternative valve system of the present invention.

Reference symbols are used in the Figures to indicate certain components, aspects or features shown therein, with reference symbols common to more than one Figure indicating like components, aspects or features shown therein.

DETAILED DESCRIPTION OF THE INVENTION

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus it is intended that the scope of the invention herein disclosed should not be limited by the particular disclosed embodiments described below. Thus, for example, in any apparatus disclosed herein, elements from different embodiments may be arranged in suitable combinations, and are not necessarily limited to any particular disclosed embodiment. In any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Disclosed herein are apparatus and methods for handing and measuring fluid materials including, but not limited to, gases, liquids, and supercritical fluids, and referred to herein without limitation as fluids. FIG. 1 is a schematic of a measurement apparatus 10 of the present invention. Measurement apparatus 10 includes a valve system 100, a passageway 109 from the valve system into a sample container 16 of a sample holder 15 that may contain a material sample M, a passageway 111 from the valve system to one or more pressure measuring devices 17, one or more temperature measuring devices 19, and a computer system 19. Valve system 100 includes one or more valves and passageways, and is used to control the passage of fluids between sample container 16 and one or more sources 12. For illustrative purposes, FIG. 1 shows source 12 as including a first source 11, a second source 13, although neither measurement apparatus 10 nor valve system 100 is limited to two sources and may, in alternative embodiments include only one source, or three or more sources.

Material sample M is, in general, any material that may exhibit pressure dependent changes including, but not limited to, a sorption material or materials to be measured for measuring bulk density, packing density, pore-size distribution, or surface area of non-sorbing materials.

As discussed subsequently, valve system 100 is operated to change the volume that encloses material sample M (and which would also preferably change the pressure within the material sample enclosing volume). In the embodiment of FIG. 1, for example, first source 11 is a source of fluid at pressure up to 3,000 psi (20.7 MPa), or alternatively up to 5,000 psi (34.5 MPa), and second source 13 is a vacuum source. Pressure measuring device 17 may be, for example, a pressure transducer such as a Model 870B Micro-Baratron® capacitance manometer (MKS Instruments, Wilmington, Mass.), pressure transducers generally described as strain-gauge pressure transducers, or piezoelectric pressure transducer, and be a gauge pressure measuring device (measures with respect to open atmosphere), absolute (measures with respect to vacuum), or differential (measures with respect to a known reference pressure).

Thus, for example, FIG. 1 shows material sample M within a volume that includes sample container 16 and passageway 109. The volume of the reservoir surrounding material sample M includes the volume of sample container 16 and passageway 109, and also includes a connected space within a portion of valve system 100 according to the operation of the valve system. Valve system 100 thus acts to change the reservoir enclosing a material sample M. In one embodiment, material sample M is contained within a first sample reservoir 30, and the action of valve system 100 acts to combine the volume of the first sample reservoir with that of a dosing reservoir 20, substantially contained within valve system 100, to form a second sample reservoir 40. In another embodiment, material sample M is contained within a second sample reservoir 40, and the action of valve system 100 acts to reduce the volume of the second sample reservoir by that of dosing reservoir 20 to form a first sample reservoir 30. Reservoirs 20, 30, and 40 are preferably either known, measured, or calibrated volumes that may be charged by a source including, but not limited to one of sources 11 or 13.

The term "source" as used herein refers to a source of a fluid or of a vacuum, without limitation unless expressly stated herein. As used herein, the term "passageway" is a broad term and is used in its ordinary sense and includes, without limitation except as explicitly stated, as any opening through a material through which a fluid may pass so as to act as a conduit. Passageways include, but are not limited to, flexible, inflexible or partially flexible tubes, bores through materials, or any other structure that can act as a conduit and any combination or connections thereof. The passageway materials or internal surfaces of passageways are preferably inert to material flowing therethrough. A passageway, as used herein, also includes separable portions that, when connected, form a passageway. In some embodiments, passageways are formed by connections that include, but are not limited to removable fittings, such as VCR fittings or bulkhead fittings, or by permanently coupling separate passageways to form longer passageway. The term "dosing reservoir" as used herein refers, without limitation and unless expressly stated herein, to an internal volume that may be used to selectively increase or decrease the volume of fluid within an internal volume of a sample holder, and thereby add or remove fluid that is in contact with the material sample. The act of combining or removing fluids using dosing reservoirs is a "dosing" operation that "doses" a material sample contained therein with a "dosing volume." The processes of sorption or desorption with the material sample depend on the change in fluid pressure at the material sample upon dosing.

In one embodiment, computer system 19 operates valve system 100 to obtain repetitive data. Thus, for example, software commands computer system 19 to simulate the manual operations that an experimenter would perform on an identical system with manual valves, and which may run for hours, days or months to obtain measurements on a material sample. Thus, for example computer system 19 may contain programming to provide aliquots to a material sample at every increasing or decreasing pressures and/or temperatures to obtain sorption data, such a PCT curve. Thus, for example, measurement apparatus 10 may control a commercial gas sorption analyzer such as PCTPro-2000 (Hy-Energy LLC, Newark, Calif.) and which is described, in part, in U.S. patent application Ser. No. 10/440,069, filed May 17, 2003, GROSS, "METHOD AND APPARATUS FOR MEASURING GAS SORPTION AND DESORPTION PROPERTIES OF MATERIALS," the contents of which are incorporated herein by reference. The automatic operation of valves is well known in the field and includes, for example, air-operated or electrically controlled devices. In an alternative embodiment, some or all of valve system 100 is manually operated.

In one embodiment, one or more of some or all of valve system 100, sample holder 15, pressure measuring device 17 and connecting passageways are in one or more independently thermally insulated enclosures that include built-in heaters and temperature measuring devices such as thermocouples, rtds, thermostats or other temperature monitoring devices for temperature control. Thus, for example, FIG. 1 shows a temperature measuring device 21 and heater or cooling elements 23 in contact with sample holder 15. In one embodiment, the material sample and sample holder 15 is temperature controlled from high temperatures (up to approximately 1000° C.) using heating elements to low temperatures such as the temperature of liquid helium or liquid nitrogen. In another embodiment, the fluid is maintained at a constant temperature slightly above room temperature by placing a portion of the valve system 100 within an insulated enclosure which is heated. In the preferred embodiment of the present invention, the heating is provided by an electric resistive enclosure heating element, however, other types of heating may also be used. The temperature is regulated using a software controller that may include PID temperature regulation, by computer system 19, or by hardware temperature controlling devices such as thermostats that supplies power to the enclosure heating element through the enclosure heating element 110 V AC output device. Feedback for the software PID controller comes from an enclosure temperature measuring device 21 inside of the enclosure containing valve system 100 or sample holder 15.

As described subsequently, measurement apparatus 10 may be used to determine effects of fluids from one or more of source 11 or 13 on material sample M with valve system 100 providing fluids, including a dose volume of known or measurable quantities of fluids, to the material sample, and performing measurements on the material sample, including but not limited to pressure or temperature measurement. Thus, for example, the fluid of first source 11 may include, but not limited to a gas, such as hydrogen gas, air, oxygen, nitrogen, krypton, argon, helium, ammonia, carbon monoxide, carbon dioxide, gaseous hydrocarbons, or methane, a liquid, such as water, acquiesce solutions, solvents, or liquid hydrocarbons; or a supercritical fluid, such as supercritical carbon dioxide, or a mixture thereof, such as humid air, or air with volatile hydrocarbons. The second source 13 is a vacuum source.

Valve system 100 provides fluid communication between two or more ports, with the embodiment of FIG. 1 having a first port 101, a second port 103, a third port 105, and a fourth port 107. Valve system 100 permits the transfer of fluids between ports, such as between either one of first port 101 (shown, for example, as arrow G) or second port 103 (shown, for example, as arrow V) and third port 105 (shown, for example, as double arrow S). In one embodiment, valve system 100 provides doses of fluids between two or more ports. Thus, for example, valve system 100 can transfer fluid or vacuum in dose reservoir 20 between port 101 and port 105, or can transfer the same or a different volume of fluid in dose reservoir 20 between port 105 and port 103. In an alternative embodiment, valve system 100 also provides direct fluid communication between selected ones of ports 101, 103 and 105 without dosing.

Valve system 100 also selectively provides fluid communication between port 107 and one or more of ports 101, 103, and 105. Pressure measuring device 17, which is connected to port 107, may thus selectively measure the pressure within sample holder 15 and one or more of first source 11 and second source 13.

Although valve system 100 is well suited for use in measurement system 10, neither the valve system, and its various component parts, or methods of operation is limited to any particular use, except as expressly stated below.

Computer system 19 controls the operation of valve system 100, such as the fluid connections, and/or the control of doses, between different ports, and also collects and stores temperature readings from temperature measuring device 21 and pressure measuring device 17. Thus, for example, computer system 19 can control the transfer of a dose of fluid—that is, an amount of fluid that is either predetermined or controlled by valve system 100, or that has an amount that may be calculated based on measurements of the properties, such as temperature or pressure, of the fluid in measurement apparatus 10 or valve system 100.

In some embodiments, it is preferred that the volume of dosing reservoir 20 is less than approximately 0.01 milliliters, less than approximately 0.05 milliliters, less than approximately 0.1 milliliters, less than approximately 0.5 milliliters, less than approximately 1.0 milliliters, less than approximately 5.0 milliliters, or less than 1.0 liters. The quantity (aliquot) of fluid in the dosing reservoir depends on the pressure, temperature and volume of the gas. It is thus advantageous to include components within measurement apparatus 10 having low internal volume including, but not limited to, electropolished stainless steel tubing having an inner diameter of, but not limited to, 0.01 inches (0.25 mm), 0.02 inches (0.50 mm), 0.04 inches (1 mm), 0.06 inches (1.5 mm), or 0.08 inches (2 mm), low-volume rotary valves, short distances, and spacers within volumes (such as within a pressure measuring device 17) to fill empty spaces to reduce internal volumes.

In a preferred embodiment, at least one of the valves of valve system 100 is a rotary valve. Rotary valves, such as Valvo injectors and valves (VICI Valco Instruments Co. Inc., Houston, Tex.) have very small internal volumes that do not change upon rotation, and are thus useful for low-volume dosing. One preferred type of rotary valve includes a small slit that conducts gas from one port on a rotary valve to the next port. To switch between gas ports on the valve, the valve is rotated until the slit is aligned with a second set of ports. Because the valve opens and closes by rotating the sealing surfaces, there is no volume change associated with opening or closing the valve. In one embodiment, the slit and all gas connections are all very small (typically on the order of 2 microliters), which is typically much smaller than the total dosing volume for making sorption measurements.

Rotary valves are known in the art having a number of ports and positions, permitting for a variety of configurations that may be used for dosing one or more samples with one or more sources. A rotary valve, in some embodiments, has the dual purpose of acting as the reservoir or part of a calibrated reservoir and the valve control device for dosing gas/liquids to a sample.

FIG. 2A is a schematic diagram of a first embodiment valve system 200 of the present invention which may be generally similar to valve system 100, except as further detailed below. Where possible, similar elements are identified with identical reference numerals.

Valve system 200 includes a first valve 202, a second valve 204, a third valve 210, having a first port 211, a second port 213, and a third port 215, each under the control of computer system 19, and passageways 201, 203, 205, 206, and 207. Passageway 201 connects port 101 and first valve 202, passageway 203 connects port 103 and second valve 202, passageway 205 connects the first and second valves to first port 211, passageway 206 connects second port 213 to port 107, and passageway 207 connects third port 215 to port 105.

First valve 202 and second valve 204 are on/off valves that are electrically controlled by computer system 19 to control fluid communication between ports 101 and 103, respectively, and third valve 210. Examples of valves 202, 204, and any other on/off valve described herein, unless otherwise stated, include, but are not limited to, pneumatic diaphragm valves, pneumatic bellows valves, needle valves, plug valves, ball valves, or any kind of motorized or electrical solenoid valves including, but not limited to, miniture solenoid, piezoelectric, mems devices or micro-fluidic valves. Third valve 210 is a three port (211, 213, and 215) valve having two positions—a first position that connects port 211 and 213, and a second position that connects port 213 and 215.

Valve system 200 may include additional valves or reservoirs. As an example, FIG. 2B shows detail of an alternative valve system 200' that is generally similar to valve systems 100 and 200, except as follows. Valve system 200' includes a valve 225 and a valve 227 in passageway 205, and a passageway 221 between valves 225 and 237 that lead to a reservoir 223 that is connected to pressure measuring device 17. Valve system 200' allows system 10 to operate, for example, as a Sieverts' device.

In one embodiment, valve 210 is a rotary valve that is controlled by computer system 19. FIGS. 3A and 3B are schematic diagrams of a first embodiment of a rotary valve 310 suitable for use as valve 210, where FIG. 3A shows rotary valve 310 in a first position 310a, and FIG. 3B shows rotary valve 310 in a second position 310b. Rotary valve 310 may be generally similar to valve 210, except as further detailed below. Where possible, similar elements are identified with identical reference numerals.

Rotary valve 310 is a three-port, two-position valve, where first position 310a connects ports 211 and 213, and second position 310b connects ports 213 and 215. More specifically, rotary valve 310 has a housing 311 with a surface 312 that on which a rotary element 313 can rotates as indicated by an arrow R. Rotary element 313 includes a passageway 315 having a first end 315a and a second end 315b. Housing 311 includes a first passageway 317 from first port 211 to an end P1 on surface 312, a second passageway 319 from second port 213 to an end P2 on surface 312, and a third passageway 321 from third port 215 to an end P3 on surface 312. Housing 311 and rotary element 313 are configured such that one or both of ends 315a, 315b either seat against surface 312, or that each end 315a, 315b aligns with one of end P1, P2, or P3, providing fluid communication with port 211, 213, or 215, respectively, and thus connecting ports 211 and 213 or ports 213 and 215. Rotary valve 310 may be for example, a Valco 4-port switching valve, Model DC4WM-HYE. In alternative embodiments, valve 310 may include additional ports and may be, for example, a four-port, three-position valve, where only three ports and two positions are used.

FIGS. 4A and 4B are schematic diagrams of a valve system 400, where rotary valve 310 is used as valve 210 of valve system 200, and which may be generally similar to valve systems 100 or 200, except as further detailed below. Where possible, similar elements are identified with identical reference numerals.

An example of the use of valve system 400 in measurement apparatus 10 for dosing follows, where first source 11 and all valves and passageways contains hydrogen gas, second source 13 is a vacuum, and material sample M is to be tested for the ability to absorb or desorb hydrogen.

FIG. 4A shows a pre-dosing configuration. Material sample M is in contact with hydrogen having contained within first sample reservoir 30, which includes the space within sample container 16 not being taken up by material sample M, and the internal volumes of passageways 109, 207, and 321. Valves 202 and 204 are operated to supply gas at a pressure that may be different from that in sample container 16. Thus, for example, with valve 202 open ("on") and valve 204 closed ("off"), hydrogen may flow from source 11 toward pressure measuring device 17 through passageways 201, 205, 317, 315, 319, 206, and 111. Alternatively, with valve 202 closed ("off") and valve 204 open ("one"), pressure measuring device 17 and the internal volume of passageways 201, 205, 317, 315, 319, 206, and 111 are evacuated. In either case, pressure measuring device 17 is capable of measuring the pressure within valve 310.

When valve 310 is to rotated to position 310b, as shown in FIG. 4B, dosing occurs by changing the amount of gas in contact with material sample M. Specifically, in addition to the gas within first sample reservoir 30, material sample M is brought into contact with the contents and volume of dosing reservoir 20, forming second sample reservoir 40 from the internal volume fluid contained within passageways 315, 319, 206, and 111, and within pressure measuring device 17 and including the first sample reservoir 30. Dosing reservoir 20 includes the internal volumes of passageways 315, 319, 206, and 111, and the internal volume within pressure measuring device 17, and thus the lengths and cross sections of the internal volumes should be kept small to have low dosing volumes. As an example 1/16 inch (1.6 mm) outer diameter electropolished stainless steel tubing with an 0.04 inch (1 mm) inner diameter. In addition to using small passageways, dosing reservoir 20 can be reduced further by filling unused internal volume within pressure measuring device 17 with solid material, such as a piece of metal placed within the unused internal volume.

Since the configuration of FIG. 4B places pressure measuring device 17 in communication with material sample M, the change in pressure may be measured as a result of dosing the sample. The change in pressure in sample container 16 can be measured and, along with the temperature and the know volume, can be used to determine the change of fluid contained within or sorbed to the surface of material sample M. Pressure measuring device 17 may thus be used for the dual purpose of measuring the pressure of the fluid aliquot before dosing to or from the sample, as in FIG. 4A, and then measuring the pressures drop/rise in the sample holder due to sorption/desorption, as in FIG. 4B.

Figure 11:
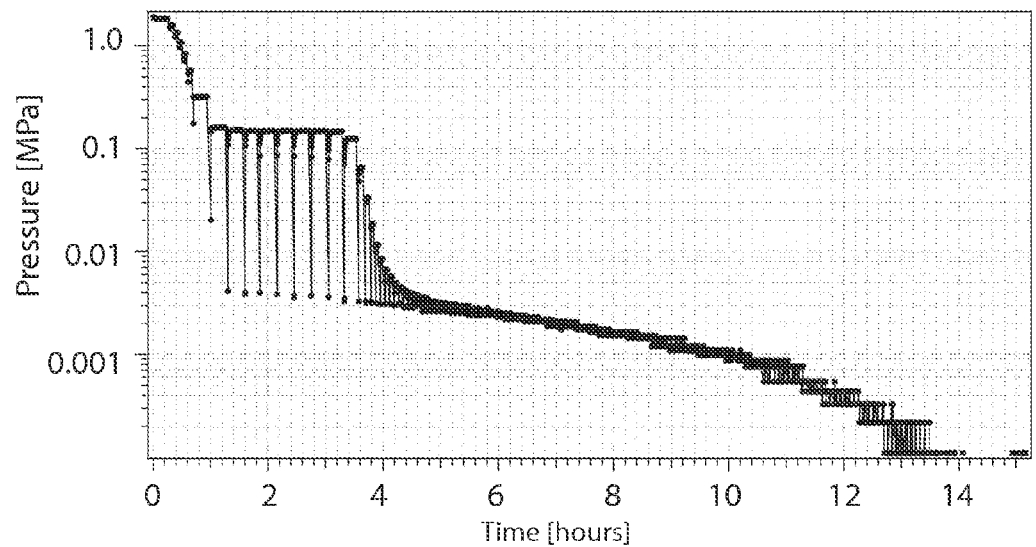
FIG. 11 is a pressure versus time plot obtained using a measurement device of the present invention.
Figure 12:
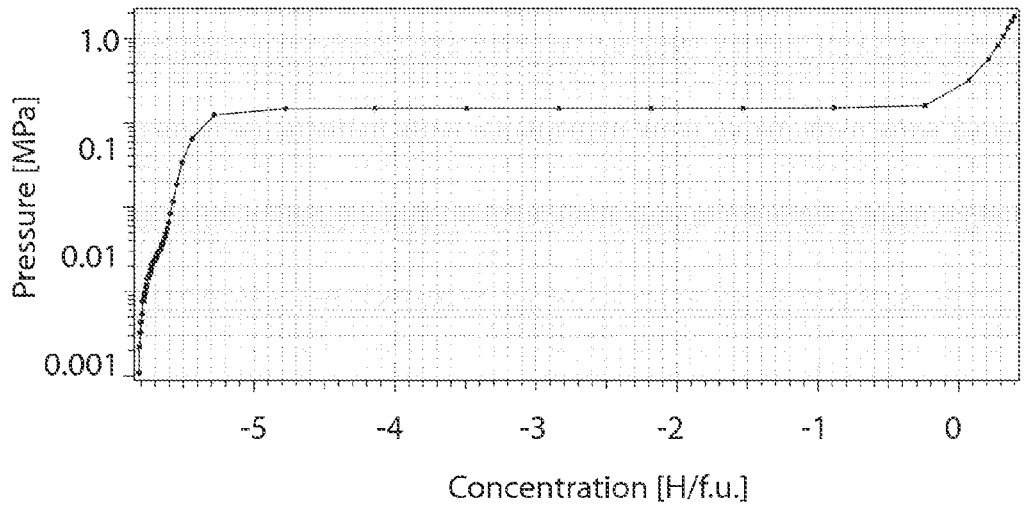
FIG. 12 is a PCT isotherm obtained using the measurements of FIG. 11.

One example of a measurement that may be performed using valve system 400 in combination with a PCTPro-2000 (a commercial gas sorption analyzer) is shown FIGS. 11 and 12. The PCTPro-2000 is programmed to use valve system 400 to execute an automated sequence of doses of gas/liquid to a sample at increasing or decreasing pressures or at a constant pressure differential with respect to a previous dose's final measured pressure. By waiting after each dose until an equilibrium sorption/desorption pressure is obtained and then measuring this pressure the quantity of gas/liquid taken up or released from the sample can be calculated. This equilibrium pressure versus the cumulative uptake or release of gas/liquid can be plotted. In the case of a gas, this plot represents and equilibrium isotherm of the gas/liquid interaction with the sample.

FIG. 11 is a pressure versus time plot obtained using a measurement device of the present invention, and FIG. 12 is a PCT isotherm obtained using the measurements of FIG. 11. The pressure of each dose is below the pressure in the sample holder causing material sample to desorption. Once the pressure in the reservoir is stabilized, the pressure is measured the quantity of gas or liquid is determined by knowing the calibration of the reservoir volume and using gas/liquid pressure-temperature-volume relationships (such as the "ideal gas law").

More specifically, FIGS. 11 and 12 show a desorption isotherm of the release of hydrogen from a sample of a single sliver of $LaNi_5$ having a mass of approximately 45 milligrams. Dosing reservoir 20 has a volume of approximately 0.5 milliliters. The pressure data collected as a function of time is shown in FIG. 11. This raw data was used to calculate the sample's gas concentration released that is plotted in the PCT isotherm shown in FIG. 12.

More specifically, the quantity of gas ad/absorbed or desorbed for each measurement, $N_j$, is given by:

$$N_j = \frac{1}{RT}\sum_j (P_{Rj}V_R + P_{j-1}V_C - P_j(V_R + V_C)) \quad \text{EQ. 1}$$

where j is the dosing step, $V_R$ is the dosing reservoir volume, $V_C$ is the sample holder internal volume, $P_{Rj}$ is the pressure measured in the dosing reservoir $V_R$ at step j when the rotary valve is in a first position and the reservoir volume is in fluid communication with the source, $P_{j-1}$ is the pressure measured in the second position inside of the second enclosed volume including the dosing reservoir and the internal volume $V_R+V_C$ at the previous measurement step j−1 where Pj−1 is then taken to be equal to the pressure inside of the first enclosed volume which is the internal volume Vc when the rotary valve is in the first position of measurement step j, $P_j$ is the pressure measured inside of the second enclosed volume including the dosing reservoir and the internal volume $V_R+V_C$ at measurement step j when the rotary valve has been rotated into the second position, R is the universal gas constant, and T is the average gas temperature. When the change in pressure finally slows to a specified limit, this pressure reading $P_j$ is taken as the equilibrium pressure $P_{Ej}$ and the calculated quantity of gas sorbed $N_j$ corresponding to the equilibrium pressure is taken as the equilibrium concentration $N_{Ej}$ sorbed or desorbed in that aliquot measurement j. For PCT measurements the process is repeated. The sum of $N_{Ej}$ is plotted versus $P_{Ej}$ to form a PCT isotherm graph. The methods by which temperature and pressure measurements are used to determine PCT isotherms are described in greater detail, for example, in U.S. patent application Ser. No. 10/440,069, filed May 17, 2003, GROSS, "METHOD AND APPARATUS FOR MEASURING GAS SORPTION AND DESORPTION PROPERTIES OF MATERIALS."

Alternative Embodiments

FIG. 5 is a schematic of an alternative valve system 500 of the present invention which may be generally similar to valve systems 100, 200 or 400, except as further detailed below. Where possible, similar elements are identified with identical reference numerals.

Valve system 500 differs from the previously described valve systems in that it includes a single fluid port, port 101, a two-port, two-position valve 510, a passageway 501 from passageway 205 to a port 107a, and a passageway 503 from passageway 207 to a port 107b. Each port 107a and 107b may be attached to a pressure measuring device 17. This embodiment permits the measure the pressure of the fluid aliquot before dosing to/from the sample (via port 107a) and the pressure drop/rise in the sample holder due to absorption (adsorption)/desorption (via port 107b).

Figure 6A:
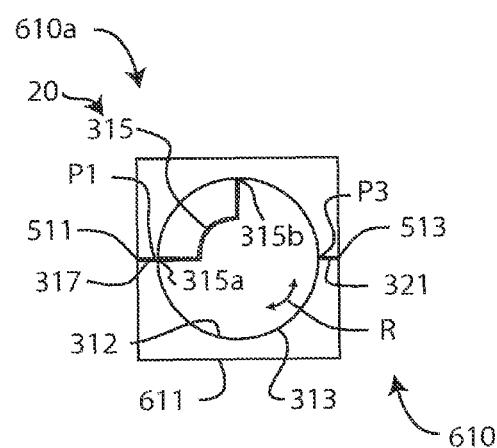
FIGS. 6A and 6B are schematic diagrams of a second embodiment of a rotary valve for use with valve systems of the present invention as a two-port, two-position valve, where
Figure 6B:
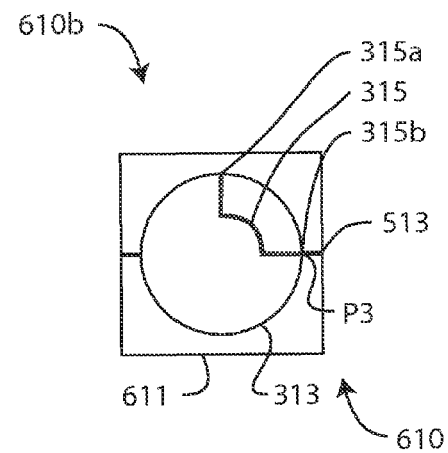

In one embodiment, valve 510 is a rotary valve. FIGS. 6A and 6B are schematic diagrams of a second embodiment of a rotary valve 610 suitable for use as valve 510, where FIG. 6A shows rotary valve 610 in a first position 610a, and FIG. 6B shows rotary valve 610 in a second position 610b. Rotary valve 610 may be generally similar to valves 210, 310, or 510, except as further detailed below. Where possible, similar elements are identified with identical reference numerals.

Rotary valve 610 has a housing 611, which is generally similar to housing 311, except that it does not have a passageway 319. Rotary valve 610 is a two-port, two-position valve, where FIG. 6A shows the rotary valve in a first position 610a and FIG. 6B shows the rotary valve in a second position 610b. The use of rotary valve 610 for valve 510 can result in a lower dosing volume, since the port for measuring pressure (such as port 213 of FIG. 2) is eliminated, further reducing the volume of dosing reservoir 20 to the volume of passageway 315 which can be, for example, less than 0.1 milliliter. Alternatively a valve 210 could be used in place of valve 610, with port 213 sealed off or provided with a sealed passageway of constant volume.

Figure 7:
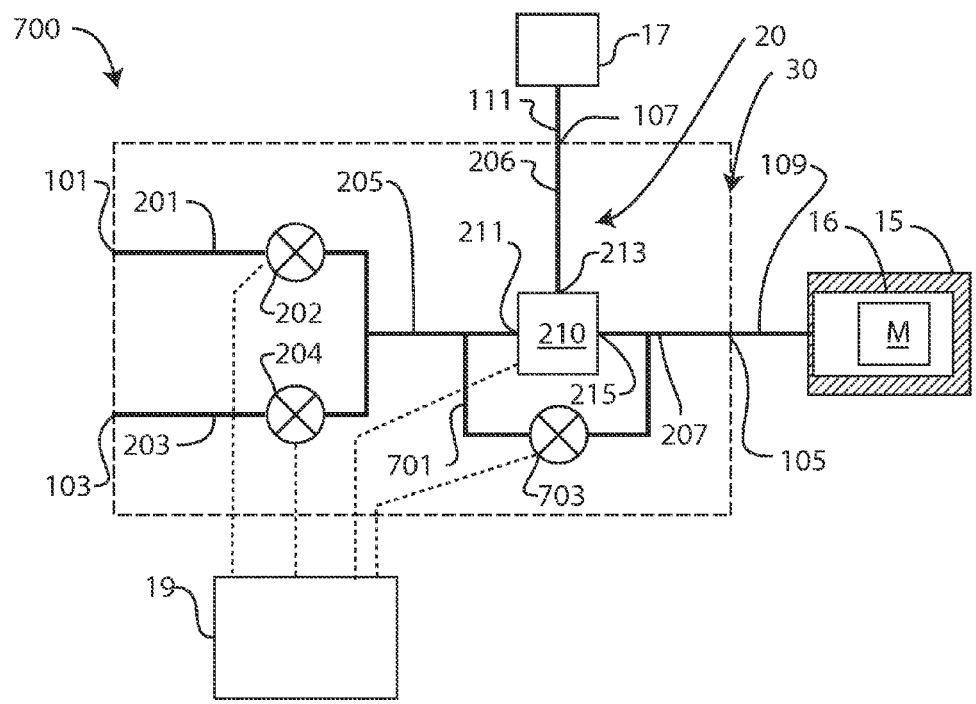
FIG. 7 is a schematic diagram of a first embodiment of a dosing/bypass valve system of the present invention.

Alternative embodiments, referred to herein as dosing/bypass valve systems, provide for both dosing and dosing bypass by providing for direct contact of port 105 and either one of ports 101 and 103. FIG. 7 is a schematic diagram of a first embodiment of a dosing/bypass valve system 700 of the present invention which may be generally similar to valve systems 100, 200, 400, or 500, except as further detailed below. Where possible, similar elements are identified with identical reference numerals.

Dosing/bypass valve system 700 includes an on/off valve 703 within a passageway 701 than connects passageways 205 and 207. Valve 703, which is controlled by computer system 19 or, alternatively, is manually operated, provides a bypass to valve 210, which may be a rotary valve. Valve system 700 is particularly useful for measurements where the material sample M must be prepared by directly exposing the sample to the fluid to a vacuum, as from one of sources 11 or 13. Thus, for example, with valve 202 and 703 open ("on") and valve 204 closed ("off"), material sample M is exposed to the fluid provided by port 101 (for example, hydrogen gas). With valve 204 and 703 open ("on") and valve 202 closed ("off"), material sample M is exposed to the fluid provided by port 103 (for example, a vacuum).

Figure 8:
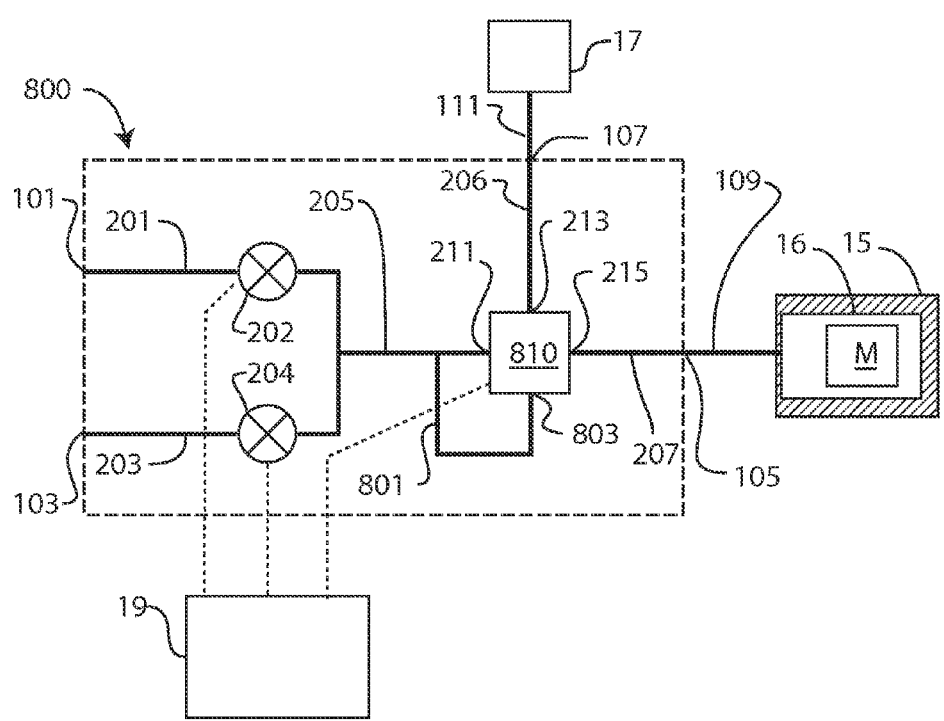
FIG. 8 is a schematic diagram of a second embodiment of a dosing/bypass valve system of the present invention.

FIG. 8 is a schematic diagram of a second embodiment of a dosing/bypass valve system 800 of the present invention which may be generally similar to valve systems 100, 200, 400, 500, or 700 except as further detailed below. Where possible, similar elements are identified with identical reference numerals.

Dosing/bypass valve system 800 includes a valve 810 having at least four ports and three positions. More specifically, valve 810 has first, second, and third ports 211, 213, and 215, respectively, and a fourth port 803, and a passageway 801 that connects passageway 205 to port 803. Valve 810, which may be generally similar to valve 210 or 510 except as noted subsequently, includes a third position that connects ports 803 and 215. As with valve 210, valve 810 has a first position that connects that connects ports 211 and 213, a second position that connects ports 213 and 215, the operation of which have been described previously, and a third position that connects ports 803 and 215 and which is useful, in measurement apparatus 10, in providing direct contact between material sample M and sources 11 or 13.

Figure 9:
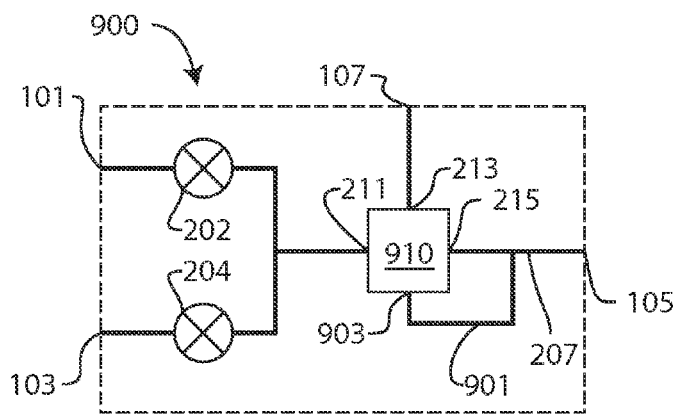
FIG. 9 is a schematic diagram of a third embodiment of a dosing/bypass valve system of the present invention.

FIG. 9 is a schematic diagram of a third embodiment of a dosing/bypass valve system 900 of the present invention which may be generally similar to valve systems 100, 200, 400, 500, 700, or 800 except as further detailed. Where possible, similar elements are identified with identical reference numerals.

Dosing/bypass valve system 900 includes a valve 910 having at least four ports and three positions. More specifically, valve 910 has first, second, and third ports 211, 213, and 215, respectively, and a fourth port 903, and a passageway 901 that connects passageway 207 to port 903. Valve 910, which may be generally similar to valve 210, 510, or 810 except as noted subsequently, includes a third position that connects ports 903 and 211. As with valve 210, and 810, valve 910 has a first position that connects that connects ports 211 and 213, a second position that connects ports 213 and 215. The third position that connects ports 903 and 211 and which is useful, in measurement apparatus 10, in providing direct contact between material sample M and sources 11 or 13.

Figures 10A, 10B:
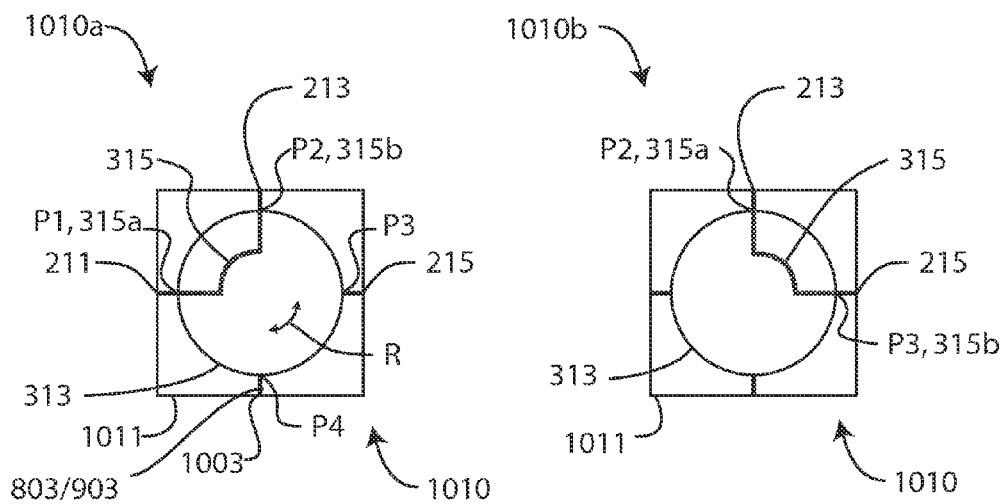
FIGS. 10A, 10B, 10C, and 10D are schematic diagrams of a third embodiment of a rotary valve for use with valve systems of the present invention as a four-port, four-position valve, where
Figures 10C, 10D:
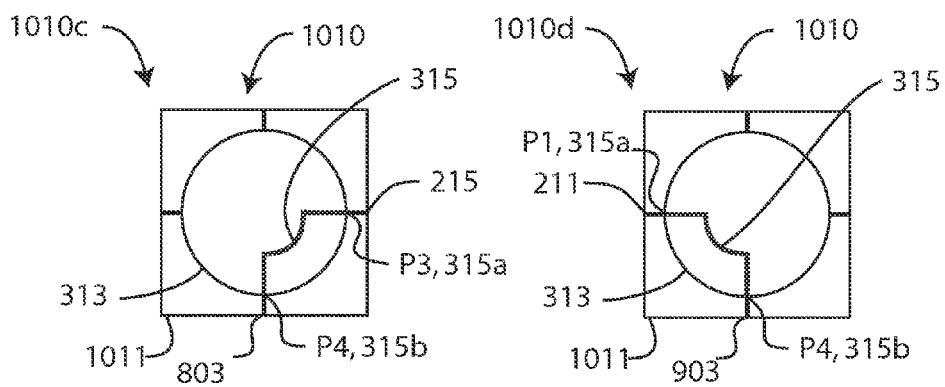

In one embodiment, valve 810 or 910 is a rotary valve. FIGS. 10A, 10B, 10C, and 10D are schematic diagrams of a third embodiment of a rotary valve 1010 suitable for use as valve 810 or 910 where FIG. 10A shows rotary valve 1010 in a first position 110a, FIG. 10B shows rotary valve 1010 in a second position 1010b, FIG. 10C shows rotary valve 1010 in a third position 1010c, and FIG. 10D shows rotary valve 1010 in a third position 1010d. Rotary valve 1010 may be generally similar to valves 210, 310, 510, 610, or 810 except as further detailed below. Where possible, similar elements are identified with identical reference numerals.

Rotary valve 1010 has a housing 1011, which is generally similar to housings 311 or 611, and includes a passageway 1001 from end P4 on surface 312 to a port labeled 803/903. Rotary valve 1010 is a four-port, four-position valve, where first position 1010a connects ports 211 and 213, second position 1010b connects ports 213 and 215, third position 1010c connects ports 215 and 803/903, and third position 1010d connects ports 211 and 803/903. Rotary valve 1010 has a housing 1011 within a surface 312 that on which a rotary element 313 can rotates as indicated by an arrow R. Housing 311 and rotary element 313 are configured such that one or both of ends 315a, 315b either seat against surface 312, or that each end 315a, 315b aligns with one of end P1, P2, P3, or P4 providing fluid communication with port 211, 213, 215, or 803/903, respectively, and thus connecting ports 211 and 213, ports 213 and 215, or ports 803/903 and 215.

Rotary valve 1010, which is a four-position valve, may be used either as valve 810 or as valve 910. For use as valve 810, the three positions of valve 810 described above correspond to positions 1010a, 1010b, and 1010c respectively. For use as valve 910, the three positions of valve 910 described above correspond to positions 1010a, 1010b, and 1010d respectively.

Alternative embodiments include using the following uses of rotary valves having multiple ports and positions include, but are not limited to: 1) a rotary valve that can connect multiple ports to multiple sample holders, enabling the measurement of sorption properties of multiple samples. Such an embodiment may either use one pressure measuring device that is sequentially placed in fluid communication with individual sample holders, or may have multiple pressure measuring devices to obtain data from multiple sample holders, or may have one pressure measuring device per sample holder. 2) A rotary valve that can connect multiple ports having different dosing reservoirs, which may be generally similar to dosing reservoir 20, to a sample holder. In one embodiment, the volume of the dosing reservoirs range from approximately 0.001 ml to approximately 1 liter, or more. These different dosing reservoirs may be selected manually or through the use of automation software, or 3) connecting multiple ports to multiple pressure measuring devices. This allows the measurement and dosing of gases or liquids over different ranges of pressures (for example 0.001 to 1.0 bar or 0.1 to 30 bar). These different pressure measuring devices may be selected manually or through the use of automation software. 4) connecting multiple ports to multiple pressure measuring devices and multiple dosing reservoir volumes. This allows the measurement and dosing of gases or liquids from a wide range of volumes (for example 0.001 ml to approximately 1 liter) over different ranges of pressures (for example 0.001 to 1.0 bar or 0.1 to 30 bar).

Figure 21:
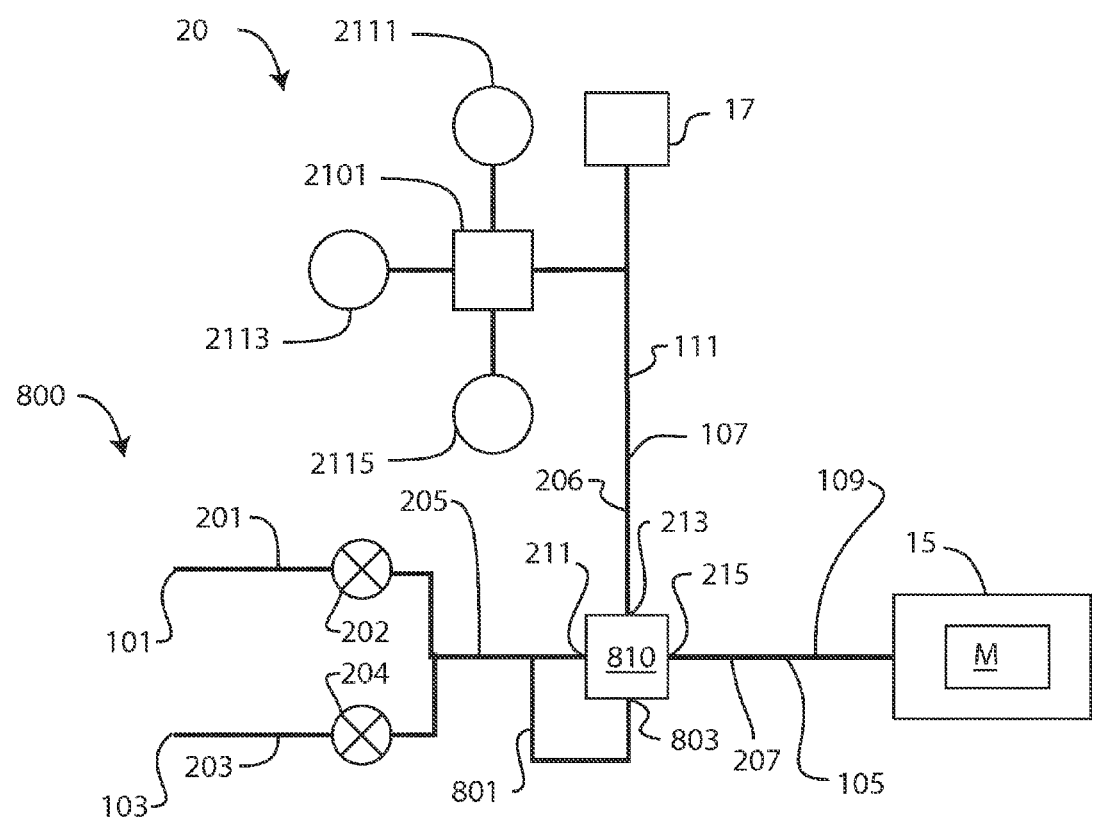
FIG. 21 is an embodiment of the invention that permits the selection of one of a number of dosing reservoirs.
Figure 22:
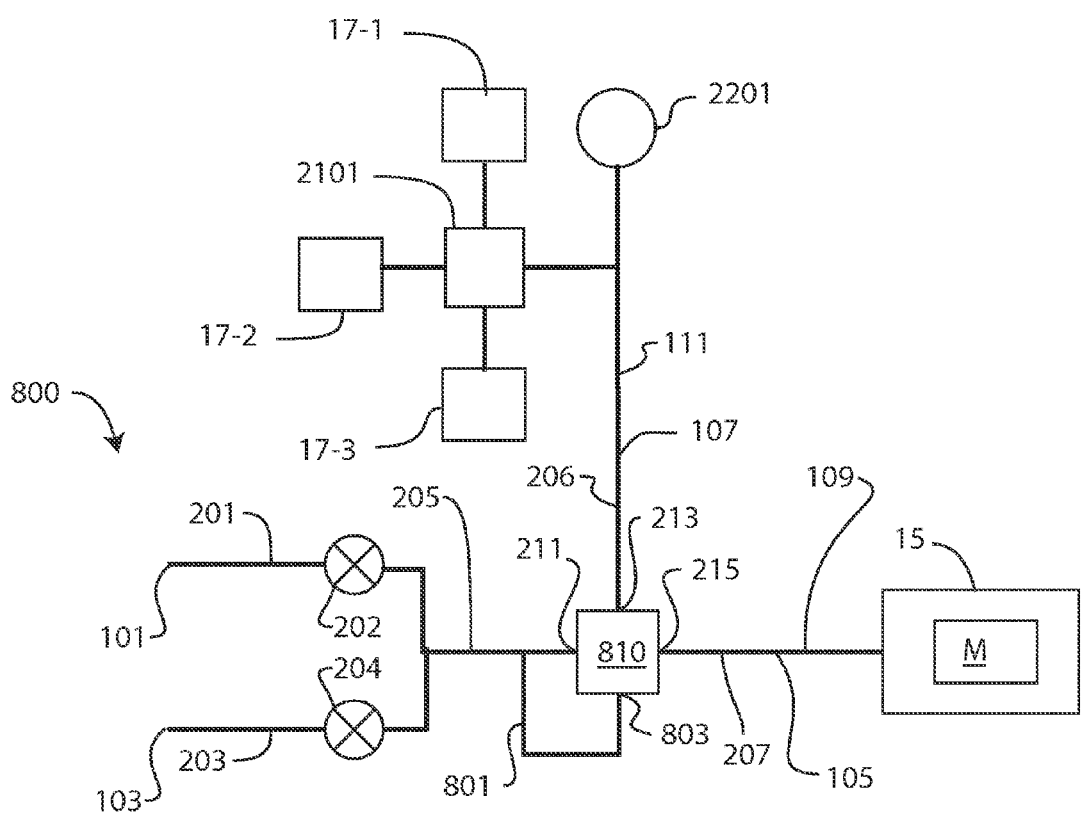
FIG. 22 is an embodiment of the invention that permits the selection of one of a number of pressure transducers.
Figure 23:
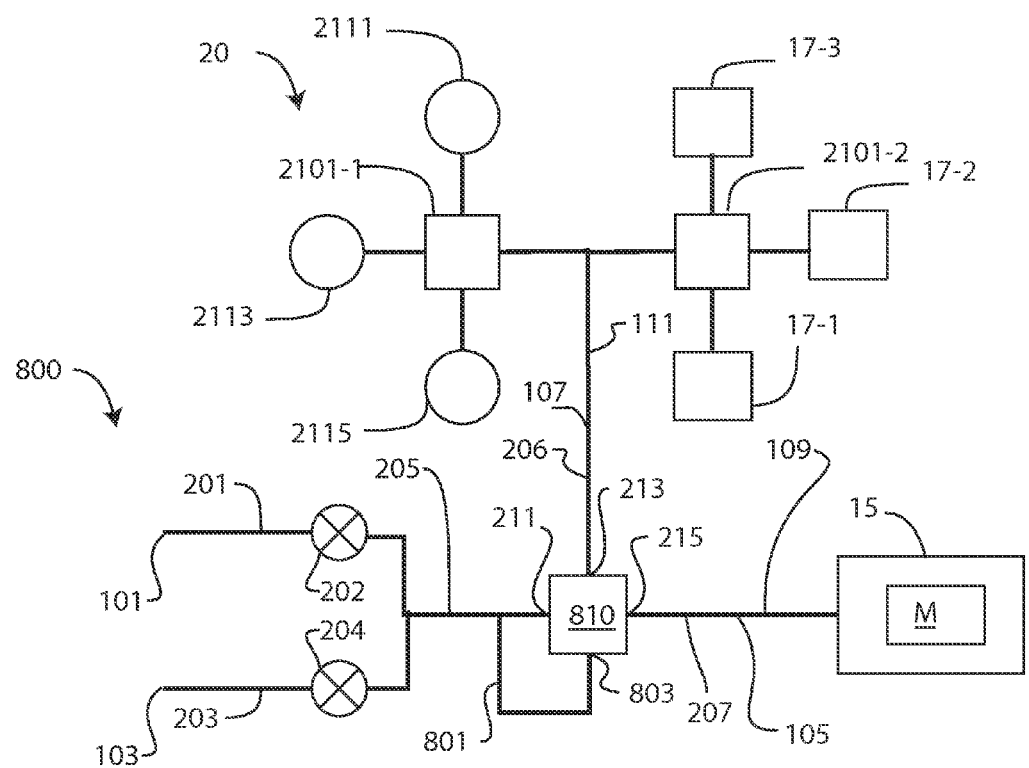
FIG. 23 is an embodiment of the invention that permits the selection of one of a number of dosing reservoirs and the selection of one of a number of pressure transducers.

Examples of some of these alternative embodiments are shown in FIG. 21 as an embodiment of the invention that permits the selection of one of a number of dosing volumes, in FIG. 22 as an embodiment of the invention that permits the selection of one of a number of pressure transducers, and FIG. 23 as an embodiment of the invention that permits the selection of one of a number of dosing volumes and the selection of one of a number of pressure transducers.

In the embodiment of FIG. 21, more than one volume may be dosed. Thus, for example, FIG. 21 shows, but the invention is not limited to, three dosing reservoirs 2111, 2113, and 2115 can be individually connected through a valve 2101 to port 213. The different volumes may be obtained, for example, by providing different lengths of closed tubing to different ports. Valve 2101 is, for example, a rotary valve or a multiport valve or a manifold having several individual on/off valves, such as solenoid valves, that provides fluid communication between one of a plurality of input ports and one output port. The volumes of dosing reservoirs 2111, 2113, and 2115 of FIG. 21 can each be different and range from 0.1 milliliter to 10.0 milliliters or more. The volumes are filled by selecting a volume via valve 2101 when ports 211 and 213 are connected. This provides a convenient method for selecting a range of doses. Valve 2101 may be manually operated or may be, for example, an electrically operated valve controlled by computer system 19.

In the embodiment of FIG. 22, more than one pressure measurement device may be used. Thus, for example, FIG. 22 shows, but the invention is not limited to, three pressure measuring devices 17-1, 17-2, and 17-3, which may each have different ranges or sensitivities, can be individually connected through a valve 2101 to port 213. The three pressure measuring devices 17-1, 17-2, and 17-3 have ranges, for example, from approximately 0-1 Torr, (0-133 Pa) from 0-1000 Torr (0-0.133 MPa), up to 100 psi (0.69 MPa), up to 250 psi (1.7 MPa), up to 1000 psi (6.9 MPa), up to 3000 psi (21 MPa), up to 5000 psi (34 MPa), or up to 10,000 psi (69 MPa). This embodiment permits increased sensitivity by changing pressure transducers during an experiment.

The embodiment of FIG. 23 combines a system having more than one dosing reservoir and more than one pressure measurement device. Thus, for example, FIG. 23 shows, but the invention is not limited to, three volumes 2111, 2113, and 2115 can be individually connected through a valve 2101-1 to port 213, and three pressure measuring devices 17-1, 17-2, and 17-3, which may each have different ranges or sensitivities, can be individually connected through a valve 2101-2 to port 213.

Rotary Valve Operation

One embodiment of the present invention includes a valve actuator that can be switched between either an automatic dosing mode or a manual bypass (charge or discharge) mode. Thus, for example, one embodiment includes a rotary valve actuator for valve system including but not limited to dosing/bypass valve systems 800 or 900. The rotary valve actuator may be, but is not limited to, an electrical or pneumatic actuator.

Figure 13:
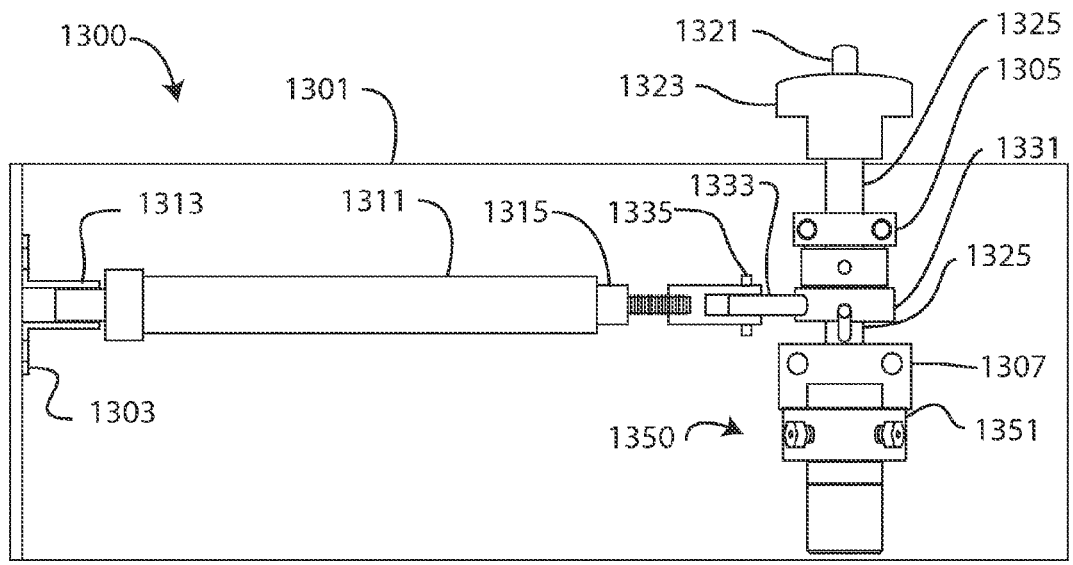
FIG. 13 is a top view of one embodiment of a rotary valve actuator of the present invention.
Figure 14:
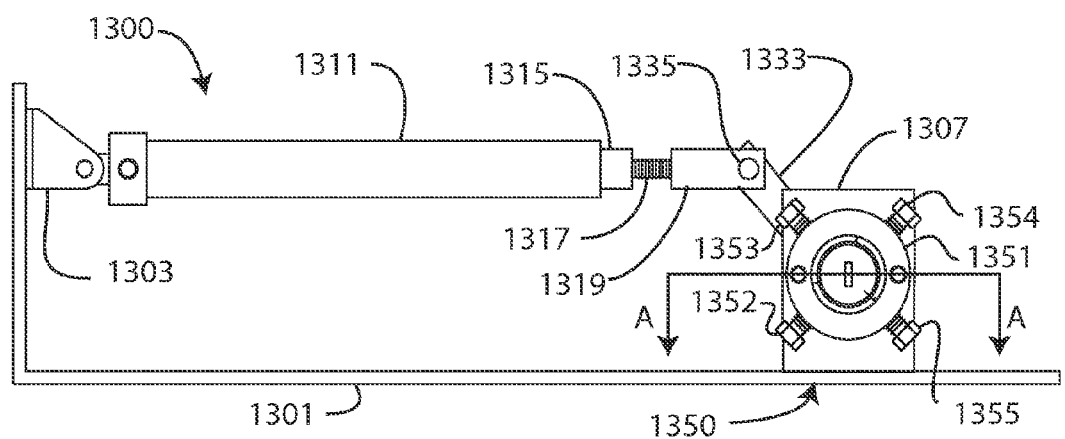
FIG. 14 is a side view of the embodiment of FIG. 13.
Figure 16A:
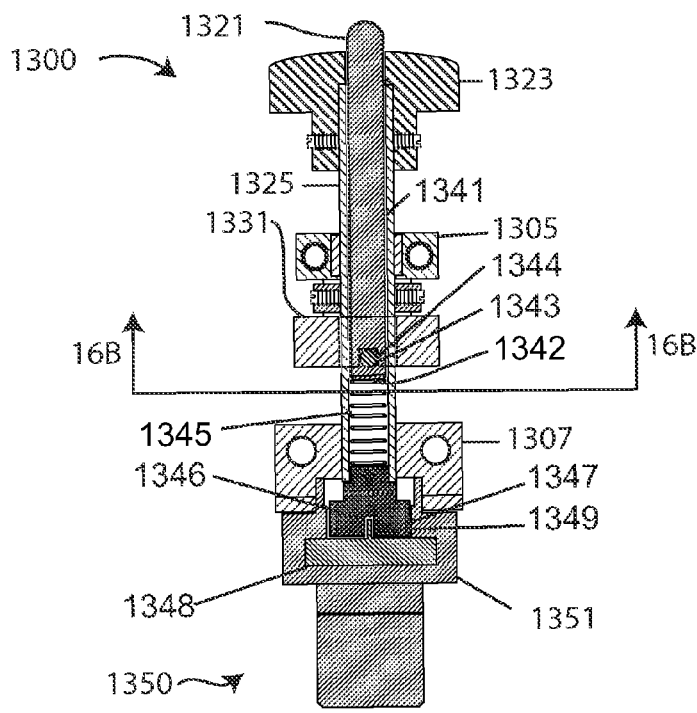
FIG. 16A is a sectional view A-A of FIG. 14 showing a rotary actuator device and rotary valve in the automatic mode in a first position.

FIGS. 13 and 14 are top and side views, respectively, of a first embodiment rotary valve actuator 1300 for operating a rotary valve 1350, and FIG. 16A is a cross-sectional view A-A of FIG. 14. Rotary valve actuator 1300 includes a pneumatic actuator 1311 and a linkage that, under the control of computer system 19, can rotate a rotary valve, including but not limited to one of rotary valves 310, 610, or 1010, through two or more valve positions.

Rotary valve actuator 1300 includes a base 1301 having a first hanger 1303, a second hanger 1307, and a third hanger 1305. Rotary valve 1350 has a rotary valve housing 1351, two or more ports, indicated as ports 1352, 1353, 1354, and 1355, and an internal rotary element 1348 having passageways connect the valve ports. Rotary valve housing 1351 is restrained by second hanger 1307.

An outer shaft 1325 is attached to rotary element 1348 by shaft adaptor 1347, extends through a linkage arm 1331 which has a transverse slot 1344 facing housing 1350, is rotatably restrained by hanger 1305, and terminates at knob 1323. Attachment of rotary element 1348 and shaft adaptor 1347 includes a slot 1346 in the shaft adaptor that accepts a tang 1349 of the rotary element. Shaft adaptor 1347 is fixed to outer shaft 1325 by a compression fit, transverse pin, or, alternatively, by a set screw (not shown). Knob 1323 is fixed to outer shaft 1325 by compression or, alternatively, by one or more set screws (not shown). Knob 1323 is thus connected to rotary element 1348. Low slip coatings or sleeves may be included to reduce friction between rotating surfaces.

An inner shaft 1341 passes through and moves longitudinally within the interior of outer shaft 1325, and extends from a button 1321 that protrudes through knob 1323 to an end 1342 proximal to valve 1350. A spring 1345 extends from shaft adapter 1347 to end 1342, providing a force on inner shaft 1341 that forces the inner shaft towards linkage arm 1331. Inner shaft 1341 has a long rotation pin 1343 mounted transverse to the inner shaft centerline and extending radially beyond the otherwise cylindrical shaft. Rotation pin 1343, which is forced by spring 1345 towards linkage arm 1331, can fit within slot 1344.

Linkage arm 1331 is attached to a linkage clevis 1333 by a rotary arm screw 1332. A cylinder rod 1315 of pneumatic actuator 1311 is threaded into a rod clevis 1319, and clevis pin 1335 forms the linkage between the pneumatic actuator and the linkage arm. Pneumatic actuator 1311, which has an air supply connection controlled by computers system 19 (not shown), is rotatably attached by pin 1313 to hanger 1303.

As described subsequently, hanger 1307 restrains rotary valve housing 1351, permitting the rotary element 1348 to rotate. Thus, for example, hanger 1307 may retrain a rotary valve housing, including but not limited to housing 311, 611, or 1011, permitting rotation of the corresponding rotary element 1348, which can be, for example, rotary element 313.

Rotary arm screw 1332 can be screwed more or less into linkage clevis 1333 to reduce or extend the length of rotary arm and therefore the radius of rotation. This length can be adjusted so that the rotation caused by pneumatic actuator 1311 matches the angular displacement required by rotary valve 1350, including, but not limited to exactly 90 degrees. In addition, cylinder rod 1315 can be screwed more or less into rod clevis 1319 to extend or reduce the longitudinal motion of the cylinder rod. This adjustment provides a means to set the position of the rotating valve so that the internal slit in the rotating valve is aligned with the ports on valve 1350.

Figure 15A:
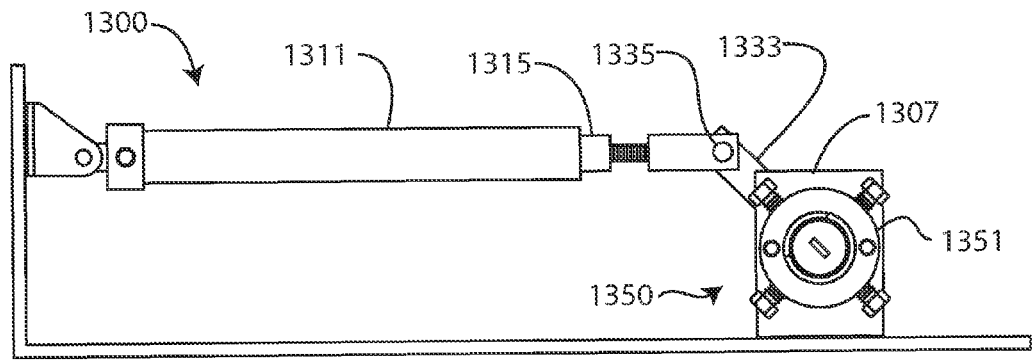
FIGS. 15A, 15B, and 15C, which show one embodiment of a rotary valve actuator at different amounts of actuation.
Figure 15B:
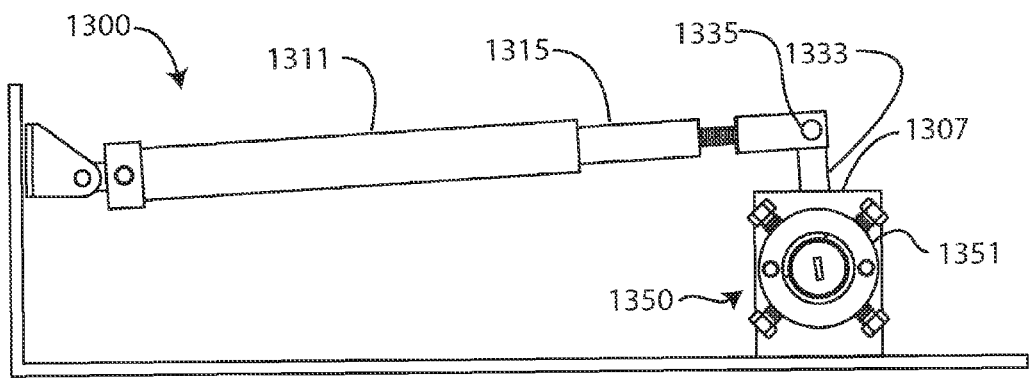
Figure 15C:
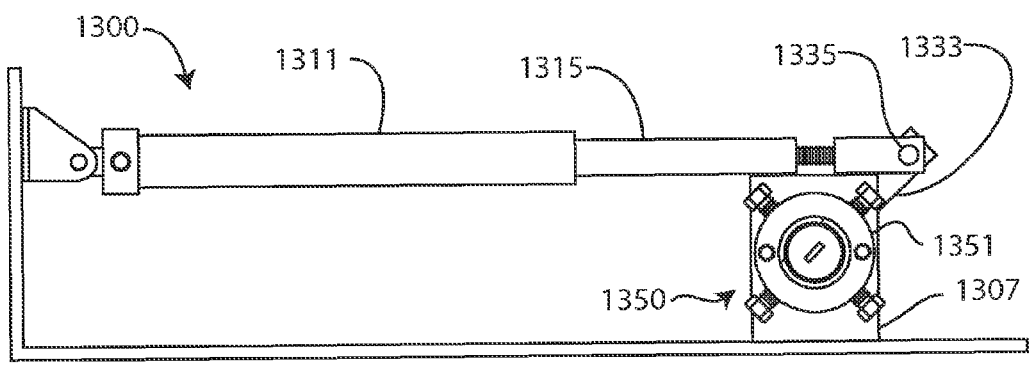

Providing pressure to pneumatic actuator 1311 results in linkage arm 1331 rotating about rotary valve 1350. The operation of pneumatic actuator 1311 is illustrated, in part, in FIGS. 15A, 15B, and 15C, which show the device 1300 at different amounts of actuation. Specifically, FIGS. 15A-15C show the actuation of pneumatic actuator 1311 at increasing amounts, such that, as cylinder rod 1315 moves increasingly outwards from the pneumatic actuator, linkage arm 1331 moves through 45 degrees. The operation of cylinder rod 1315 (and therefore rotary valve 1350) is automated through the use of computer software within computer system 19, in communications with a digital control device that opens and closes an air-operated valve that provides or releases air from the cylinder. Air pressure can be between 10 and 200 psi. When the gas pressure to the cylinder rod 1315 is relieved, a return spring (not shown) inside (or outside) of the cylinder rod causes the cylinder rod to return to its original position. Likewise through the reverse action just described above the rotating valve and all connected components rotate 90 degrees back to the original position.

Operation of the Pneumatic Rotary Valve Actuator

As described subsequently, rotary valve actuator 1300 has two modes of operation that are controlled by the position of button 1321. With button 1321 in the "out" position (that is, away from rotary valve 1350), rotary valve actuator 1300 is in a first, "automatic," mode of operation, where the operation of rotary valve 1350 is operably attached to, and controlled by, pneumatic actuator 1311. In the first mode of operation, linkage arm 1331 is operably connected to rotary element 1348, and changing the pressure of a fluid within pneumatic actuator 1311 causes a portion of rotary valve 1350 to move from one position to another as shown, for example, as the arrow R in FIGS. 3A, 6A and 10A. With button 1321 in an "in" position (that is, pushed in towards rotary valve 1350), rotary valve actuator 1300 is an a second, "manual," mode of operation, where linkage arm 1331 is disengaged from rotary valve

1350, permitting manual operation of the rotary valve which may occur, for example, by rotating knob 1323.

Figure 16B:
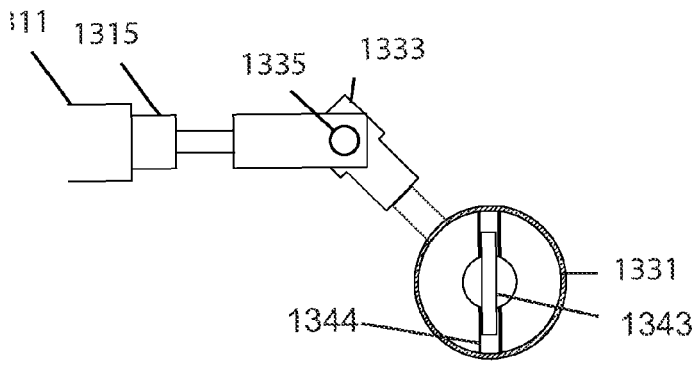
FIG. 16B is a sectional 16B-16B from FIG. 16A.
Figure 16C:
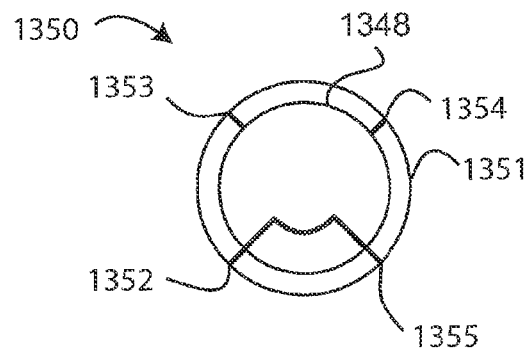
FIG. 16C is a schematic of the rotary valve.
Figure 17A:
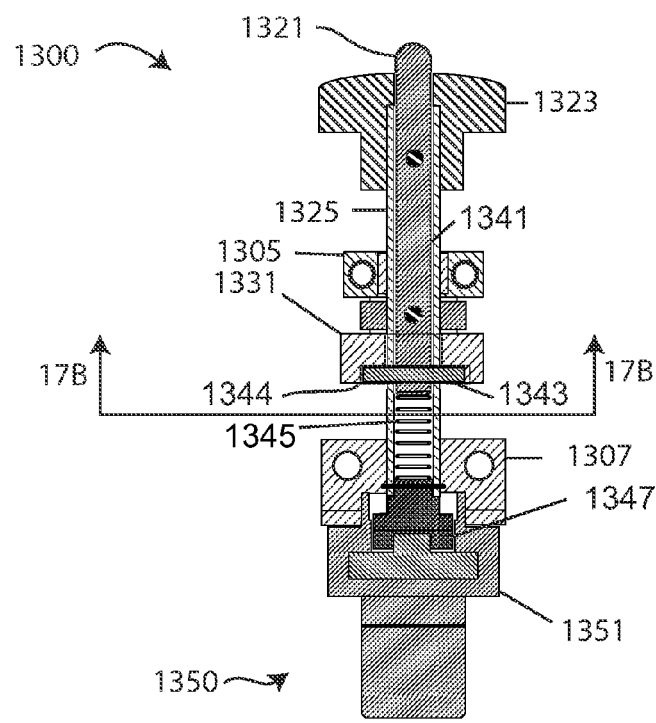
FIG. 17A is a sectional view A-A of FIG. 14 showing a rotary actuator device and rotary valve in the automatic mode in a second position.

The automatic operation of valve 1350 is illustrated with reference to FIGS. 15A, 15B and 15C, FIGS. 16A, 16B, and 16C, and FIGS. 17A, 17B, and 17C. FIG. 16A is a sectional view A-A of FIG. 14 showing rotary actuator device 1300 and rotary valve 1350 in the automatic mode in a first position, FIG. 16B is a sectional 16B-16B from FIG. 16A, and FIG. 16C is a schematic of valve 1350. FIG. 17A is a sectional view A-A of FIG. 14 showing rotary actuator device 1300 and rotary valve 1350 in the automatic mode in a second position, FIG. 17B is a sectional 17B-17B from FIG. 17A, and FIG. 17C is a schematic of valve 1350.

In the position of FIGS. 16A-16C, button 1321 is in a full "out" position, and rotation pin 1343 is engaged with transverse slot 1344. Pneumatic actuator 1311 is thus linked with rotary element 1348. Pneumatic actuator 1311 is in the retracted position of FIG. 15A, and rotary element 1348 connects ports 1352 and 1355.

Figure 17B:
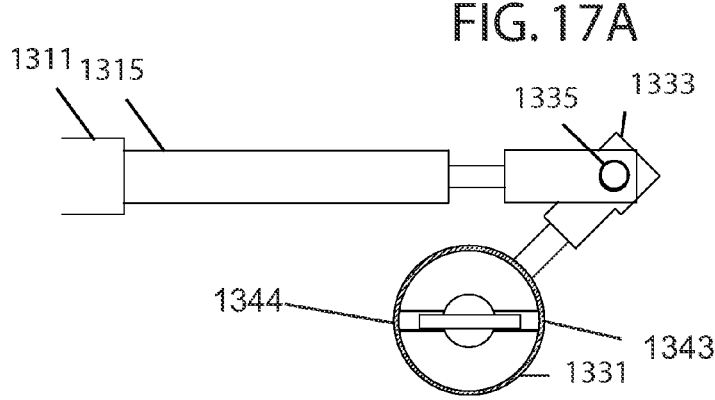
FIG. 17B is a sectional 17B-17B from FIG. 17A.
Figure 17C:
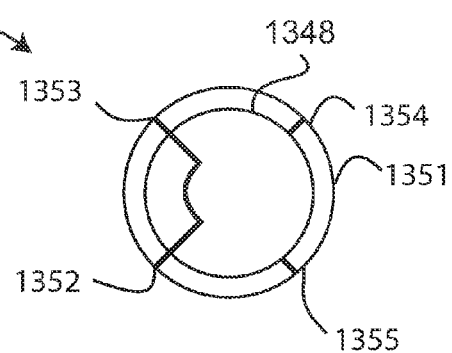
FIG. 17C is a schematic of the rotary valve.

In the position of FIGS. 17A-17C, button 1321 is in a full "out" position, and rotation pin 1343 is engaged with transverse slot 1344, as in FIGS. 16A-16C. Pneumatic actuator 1311 is in the extended position of FIG. 15C, rotating outer shaft 1325 and rotary element 1348 by 90 degrees, and thus connecting ports 1352 and 1353.

By pressing in button 1321, rotary valve 1350 may be operated in a manual mode, independent of rotary valve actuator 1300. To switch to manual mode, the operator pushes in button 1321. Rotation pin 1343 thus moves out of transverse slot 1344, disengaging linkage arm 1331. (Transverse slot 1344 and the portion of linkage arm 1331 near the transverse slot are above and below the plane of sectional views of FIGS. 16B, 17B, 18B, 19B, and 20B, and are indicated with dashed lines in those Figures). With linkage arm 1331 disengaged from outer shaft 1325, rotary valve 1350 is free to rotate to any position by turning knob 1323. Spring 1345 pushes against inner shaft 1341 so that when knob 1323 is turned to align rotation pin 1343 and transverse slot 1344, for example by returning the knob to the original position or by rotating through 180 degrees, rotation pin 1343 will again move into transverse slot 1344 when button 1321 is not being pushed in. When button 1321 not being pushed in, rotation pin 1343 is forced into transverse slot 1344 by spring 1345 engaging outer shaft 1325 with linkage arm 1331, and thus returning rotary valve 1350 to automatic mode.

Figure 18A:
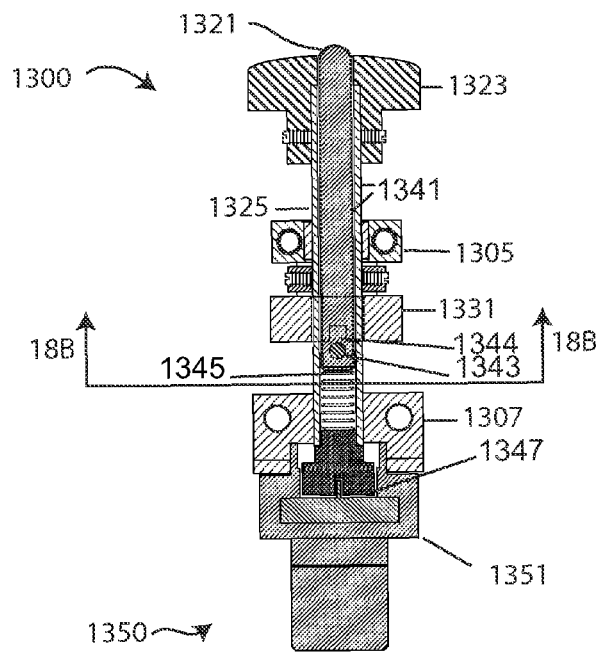
FIG. 18A is a sectional view A-A of FIG. 14 showing a rotary actuator device and rotary valve being switched to a manual mode in the first position of FIG. 16.
Figure 18B:
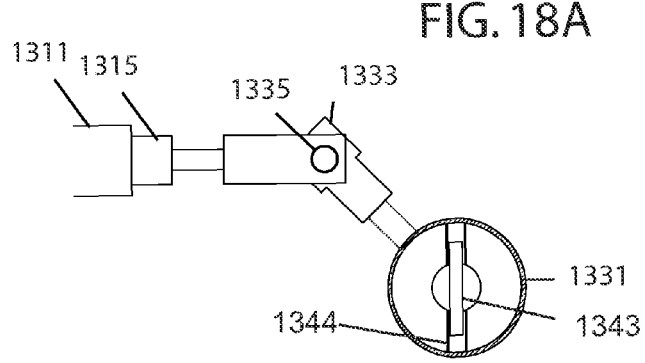
FIG. 18B is a sectional 18B-18B from FIG. 18A.
Figure 18C:
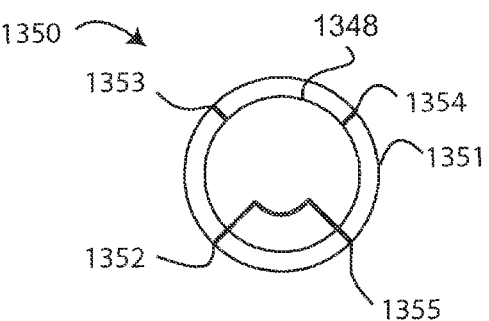
FIG. 18C is a schematic of the rotary valve.
Figure 19A:
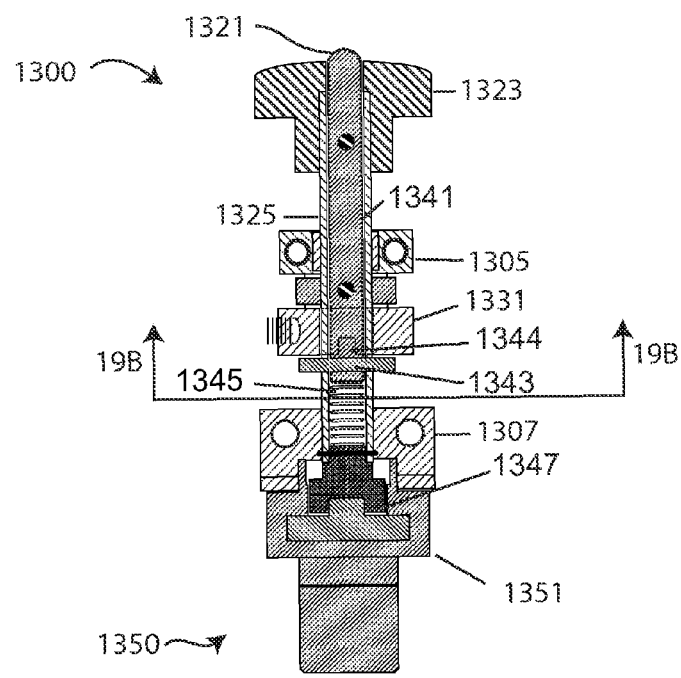
FIG. 19A is a sectional view A-A of FIG. 14 showing a rotary actuator device and rotary valve switched to a second position in the manual mode.
Figure 19B:
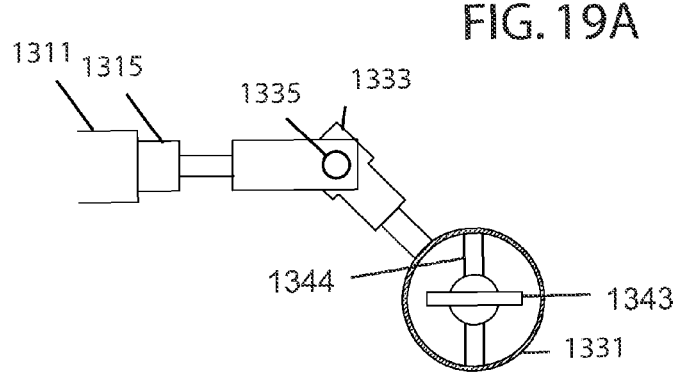
FIG. 19B is a sectional 19B-19B from FIG. 19A.
Figure 19C:
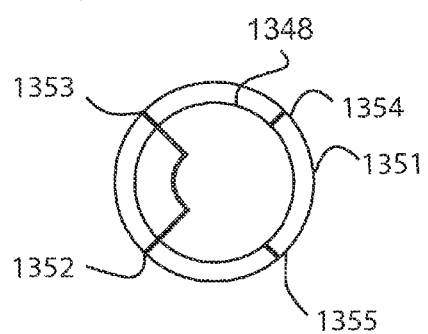
FIG. 19C is a schematic of the rotary valve.
Figure 20A:
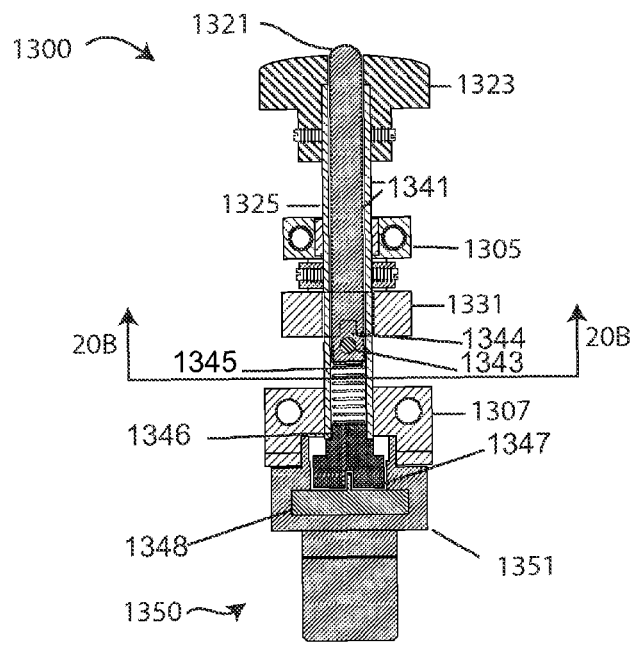
FIG. 20A is a sectional view A-A of FIG. 14 showing a rotary actuator device and rotary valve switched to a third position and reengaged in the automatic mode.

The manual operation of valve 1350 is illustrated with reference to FIGS. 15A, 15B and 15C, FIGS. 18A, 18B, and 18C, FIGS. 19A, 19B, and 19C, and FIGS. 20A, 20B, and 20C. FIG. 18A is a sectional view A-A of FIG. 14 showing rotary actuator device 1300 and rotary valve 1350 being switched to a manual mode in the first position of FIG. 16, FIG. 18B is a sectional 18B-18B from FIG. 18A, and FIG. 18C is a schematic of valve 1350. FIG. 19A is a sectional view A-A of FIG. 14 showing rotary actuator device 1300 and rotary valve 1350 switched to a second position in the manual mode, FIG. 19B is a sectional 19B-19B from FIG. 19A, and FIG. 19C is a schematic of valve 1350. FIG. 20A is a sectional view A-A of FIG. 14 showing rotary actuator device 1300 and rotary valve 1350 switched to a third position and reengaged in the automatic mode, FIG. 20B is a sectional 20B-20B from FIG. 20B, and FIG. 20C is a schematic of valve 1350.

In the position of FIGS. 18A-18C, pneumatic actuator 1311 and valve 1350 are in the first position of FIG. 16, and button 1321 is being pushed by a user (not shown) into a full "in" position, causing rotation pin 1343 to be out of transverse slot 1344, and thus disengaging outer shaft 1325 and linkage arm 1331. Pneumatic actuator 1311 is thus disengaged from rotary element 1348, and valve 1350 can be operated by rotating knob 1323.

In the position of FIGS. 19A-19C, knob 1323 has been rotated 90 degrees. Pneumatic actuator 1311 and linkage arm 1331 remain in the same position as in FIG. 18, while rotating pin 1343 and transverse slot 1344 are at 90 degrees, with the rotating pin rigidly fixed on the end of inner shaft 1341. Valve 1350 is in a position connecting ports 1352 and 1353.

Figure 20B:
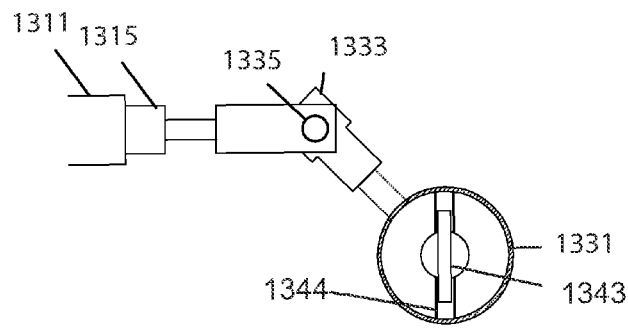
FIG. 20B is a sectional 20B-20B from FIG. 20A.
Figure 20C:
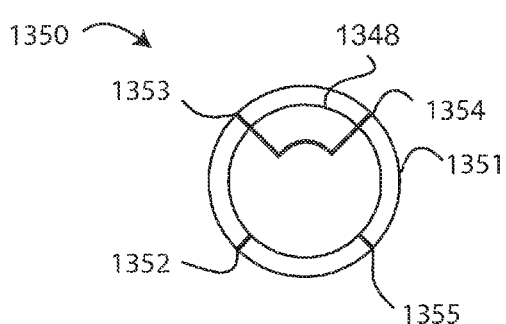
FIG. 20C is a schematic of the rotary valve.

In the position of FIGS. 20A-20C, knob 1323 has been further rotated an additional 90 degrees, aligning rotating pin 1343 and transverse slot 1344. Button 1321 is being pushed against spring 1345 and, upon release, rotating pin 1343 will be forced into transverse slot 1344, engaging pneumatic actuator 1311 and linkage arm 1331, returning valve 1350 into automatic mode. While pneumatic actuator 1311 remains in the same position as in FIG. 18, the valve has been rotated by 180 degrees, connecting ports 1353 and 1354.

Alternative embodiments of rotary valve actuator 1300 include, but are not limited to: different lengths of cylinders and rotary arm screws that can be used to provide a means to rotate the rotating valve other exact angles besides 90 degrees (useful if some valve other than a 4 port valve is desired to be used); a linkage with multiple slits at even or at not even angular spacing to provide a multitude of different actuator modes or positions using a multiport valve; a pneumatic cylinder that is a forward acting or return acting or double acting types; a pneumatic cylinder that is mounted to the right or to the left of the rotary valve actuator; and other devices to actuate the valve apparatus including, but not limited to, rotating pneumatic devices and linear motors.

In addition to the uses of the present invention described herein, low volume dosing is useful for making may types of measurements including, but not limited to: desorption concentration measurements, kinetics measurements, sorption capacity measurements, pressure-concentration-temperature isotherm measurements, cycle-life measurements, porosity measurements, surface area measurements, density measurements, diffusion measurements, enthalpy of sorption or reaction measurements, entropy of sorption or reaction measurements, phase transition analysis measurements, activation energy measurements, moisture sorption measurements, interactions of pharmaceutical chemicals or packaging materials with moisture and gases, hydrate and solvate sorption measurements, stability, chemical reactivity, dissolution rate, and density of polymorphic forms of materials, Deliquescence and hygroscopicity measurements, desorption concentration measurements, kinetics measurements, and cycle-life measurements.

One embodiment of each of the methods described herein may include a computer program that executes on a processing system, e.g., a one or more processors and memories that are part of an embedded system. Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, a game machine cartridge, or an optical storage device such as a CD-ROM.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the invention requires more features than are expressly described herein. Rather, inventive aspects lie in less than all features of a single foregoing disclosed embodiment.

Thus, while there has been described several embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

I claim:

1. An apparatus connectable to a source of fluid or vacuum, the apparatus comprising:
   a pressure measuring device;
   a sample holder having an internal volume; and
   a first valve having at least two positions, wherein the first valve includes:
   a first port fluidly connectable to the source, and
   a second port fluidly connectable to the internal volume, wherein the at least two positions of the first valve include:
      a first position that fluidly connects the first port and the pressure measuring device and defines a first enclosed volume, and
      a second position that fluidly connects the second port and the pressure measuring device and defines a second enclosed volume that includes the first enclosed volume.

2. The apparatus of claim 1, wherein the first valve further includes a third port fluidly connectable to the pressure measuring device.

3. The apparatus of claim 1, further comprising a system to control the pressure measuring device.

4. The apparatus of claim 1, wherein the pressure measuring device includes a plurality of pressure measuring devices and one or more other valves to fluidly connect each of the plurality of pressure measuring devices to the internal volume.

5. The apparatus of claim 4, wherein the plurality of pressure measuring devices includes:
   a first pressure measuring device fluidly connectable to the first valve and configured to measure a pressure associated with the first enclosed volume when the first valve is in the first position; and
   a second pressure measuring device fluidly connectable to the first valve and configured to measure a pressure associated with the second enclosed volume when the first valve is in the second position.

6. The apparatus of claim 1, wherein the pressure measuring device is included in a dosing reservoir that has a volume of less than 0.1 milliliters.

7. The apparatus of claim 1, wherein the pressure measuring device is included in a dosing reservoir that has a volume between 0.1 milliliters and 10 milliliters.

8. The apparatus of claim 1, wherein the pressure measuring device is included in a dosing reservoir, wherein the first valve charges the dosing reservoir from the source when the first valve is in the first position.

9. The apparatus of claim 1, wherein the fluid is a gas.

10. An apparatus connectable to a source of fluid or vacuum, the apparatus comprising:
    a pressure measuring device;
    a sample holder having an internal volume; and
    a first valve having at least three positions, wherein the valve includes:
    a first port fluidly connectable to the source,
    a second port fluidly connectable to the internal volume, and
    a third port fluidly connectable to the source, wherein the at least three positions of the first valve include:
       a first position that fluidly connects said first port and the pressure measuring device and defines a first enclosed volume,
       a second position that fluidly connects the second port and the pressure measuring device and defines a second enclosed volume that includes the first enclosed volume, and
       a third position that fluidly connects the third port and the internal volume.

11. The apparatus of claim 10, wherein the first valve further includes a fourth port fluidly connectable to the pressure measuring device.

12. The apparatus of claim 10, further comprising a system to control the pressure measuring device.

13. The apparatus of claim 10, wherein the pressure measuring device includes a plurality of pressure measuring devices and one or more other valves to fluidly connect each of the plurality of pressure measuring devices to the internal volume.

14. The apparatus of claim 10, wherein the pressure measuring device is included in a dosing reservoir that has a volume of less than 0.1 milliliters.

15. The apparatus of claim 10, wherein the pressure measuring device is included in a dosing reservoir that has a volume between 0.1 milliliters and 10 milliliters.

16. The apparatus of claim 10, wherein the pressure measuring device is included in a dosing reservoir, wherein the first valve charges the dosing reservoir from the source when the first valve is in the first position.

17. The apparatus of claim 10, wherein the fluid is a gas.

18. The apparatus of claim 1, further including an actuator operably engageable with the first valve.

19. The apparatus of claim 18, where the actuator includes a manual override to disengage the actuator and permit manual operation of the first valve.

20. The apparatus of claim 18, where the actuator is a pneumatic actuator.

21. The apparatus of claim 1, further including a system to control the temperature of the sample holder.

22. The apparatus of claim 1, further including a system to control the temperature of the first valve.

23. The apparatus of claim 1, further including a computer system programmed to measure sorption or desorption properties of a material sample in the sample holder.

24. The apparatus of claim 1, where the first valve is a rotary first valve.

25. The apparatus of claim 10, further including an actuator operably engageable with the first valve.

26. The apparatus of claim 25, where the actuator includes a manual override to disengage the actuator and permit manual operation of the first valve.

27. The apparatus of claim 25, where the actuator is a pneumatic actuator.

28. The apparatus of claim 10, further including a system to control the temperature of the sample holder.

29. The apparatus of claim 10, further including a system to control the temperature of the first valve.

30. The apparatus of claim 10, further including a computer system programmed to measure sorption or desorption properties of a material sample in the internal volume.

31. The apparatus of claim 10, where the first valve is a rotary valve.

* * * * *